United States Patent
Peterson et al.

(10) Patent No.: US 11,648,109 B2
(45) Date of Patent: May 16, 2023

(54) BALLOON EXPANDABLE FRAME FOR TRANSCATHETER IMPLANTATION OF A CARDIAC VALVE PROSTHESIS

(71) Applicant: MEDTRONIC, INC., Minneapolis, MN (US)

(72) Inventors: Justin Peterson, Santa Rosa, CA (US); Justin Goshgarian, Santa Rosa, CA (US); Stuart Kari, Windsor, CA (US); Tracey Tien, Tustin, CA (US); Michael Krivoruchko, Forestville, CA (US); Yas Neuberger, Santa Rosa, CA (US)

(73) Assignee: MEDTRONIC, INC., Minneapolis, MN (US)

( * ) Notice: Subject to any disclaimer, the term of this patent is extended or adjusted under 35 U.S.C. 154(b) by 218 days.

(21) Appl. No.: 16/778,688

(22) Filed: Jan. 31, 2020

(65) Prior Publication Data
US 2020/0246141 A1    Aug. 6, 2020

Related U.S. Application Data

(60) Provisional application No. 62/880,879, filed on Jul. 31, 2019, provisional application No. 62/801,041, filed on Feb. 4, 2019.

(51) Int. Cl.
*A61F 2/24* (2006.01)
*A61F 2/95* (2013.01)

(52) U.S. Cl.
CPC .......... *A61F 2/2418* (2013.01); *A61F 2/2433* (2013.01); *A61F 2/9522* (2020.05); *A61F 2250/001* (2013.01)

(58) Field of Classification Search
CPC .... A61F 2/2418; A61F 2/2433; A61F 2/9522; A61F 2250/001; A61F 2230/0006;
(Continued)

(56) References Cited

U.S. PATENT DOCUMENTS

| 5,330,500 A | 7/1994 | Song |
| 5,411,552 A | 5/1995 | Andersen et al. |

(Continued)

FOREIGN PATENT DOCUMENTS

| WO | 2003011195 A2 | 2/2003 |
| WO | 20060127765 A1 | 11/2006 |

(Continued)

OTHER PUBLICATIONS

PCT/US2020/016223, The International Search Report and Written Opinion, dated Jul. 1, 2020, 15 pgs.

*Primary Examiner* — Suzette J Gherbi
(74) *Attorney, Agent, or Firm* — Medler Ferro Woodhouse & Mills PLLC

(57) ABSTRACT

A transcatheter valve prosthesis includes a balloon expandable stent and a prosthetic valve. An inflow portion of the stent includes a plurality of crowns and a plurality of struts with each crown being formed between a pair of opposing struts. Endmost inflow side openings and endmost inflow crowns are formed at the inflow end of the stent and the inflow end of the stent has a total of twelve endmost inflow crowns. An outflow portion of the stent includes a plurality of crowns and a plurality of struts with each crown being formed between a pair of opposing struts. Endmost outflow crowns are formed at the outflow end of the stent and the outflow end of the stent has a total of six endmost outflow crowns. The prosthetic valve is disposed within and secured to the stent.

13 Claims, 22 Drawing Sheets

(58) Field of Classification Search
CPC ...... A61F 2230/0069; A61F 2250/0036; A61F 2230/0054
See application file for complete search history.

(56) References Cited

U.S. PATENT DOCUMENTS

| | | | |
|---|---|---|---|
| 5,840,081 A | 11/1998 | Andersen et al. | |
| 5,931,969 A | 8/1999 | Carpentier et al. | |
| 6,168,614 B1 | 1/2001 | Andersen et al. | |
| 6,210,957 B1 | 4/2001 | Carpentier et al. | |
| 6,214,054 B1 | 4/2001 | Cunanan et al. | |
| 6,458,153 B1 | 10/2002 | Bailey | |
| 6,547,827 B2 | 4/2003 | Carpentier et al. | |
| 6,561,970 B1 | 5/2003 | Carpentier et al. | |
| 6,582,462 B1 | 6/2003 | Andersen et al. | |
| 6,730,118 B2 | 5/2004 | Spenser et al. | |
| 6,830,584 B1 | 12/2004 | Seguin | |
| 6,893,460 B2 | 5/2005 | Spenser et al. | |
| 6,908,481 B2 | 6/2005 | Cribier | |
| 7,018,406 B2 | 3/2006 | Seguin et al. | |
| 7,198,646 B2 | 4/2007 | Figulla et al. | |
| 7,201,772 B2 | 4/2007 | Schwammenthal et al. | |
| 7,214,344 B2 | 5/2007 | Carpentier et al. | |
| 7,252,682 B2 | 8/2007 | Seguin | |
| 7,329,278 B2 | 2/2008 | Seguin et al. | |
| 7,393,360 B2 | 7/2008 | Spenser et al. | |
| 7,429,269 B2 | 9/2008 | Schwammenthal et al. | |
| 7,442,204 B2 | 10/2008 | Schwammenthal et al. | |
| RE40,570 E | 11/2008 | Carpentier et al. | |
| 7,470,285 B2 | 12/2008 | Nugent et al. | |
| 7,510,575 B2 | 3/2009 | Spenser et al. | |
| 7,530,253 B2 | 5/2009 | Spenser et al. | |
| 7,585,321 B2 | 9/2009 | Cribier | |
| 7,618,446 B2 | 11/2009 | Andersen et al. | |
| 7,682,390 B2 | 3/2010 | Seguin | |
| 7,780,723 B2 | 8/2010 | Taylor | |
| 7,780,726 B2 | 8/2010 | Seguin | |
| 7,789,909 B2 | 9/2010 | Andersen et al. | |
| 7,846,203 B2 | 12/2010 | Cribier | |
| 7,993,394 B2 | 8/2011 | Hariton et al. | |
| 8,163,011 B2 | 4/2012 | Rankin | |
| 8,236,045 B2 | 8/2012 | Benichou et al. | |
| 9,089,422 B2 | 7/2015 | Ryan et al. | |
| 9,901,447 B2 | 2/2018 | Braido et al. | |
| 9,943,407 B2 | 4/2018 | Tuval et al. | |
| 10,058,420 B2 | 8/2018 | Levi | |
| 2006/0178740 A1 | 8/2006 | Stacchino et al. | |
| 2006/0259137 A1 | 11/2006 | Artof et al. | |
| 2007/0078510 A1 | 4/2007 | Ryan | |
| 2007/0270944 A1 | 11/2007 | Bergheim et al. | |
| 2008/0154355 A1 | 6/2008 | Benichou et al. | |
| 2009/0192591 A1 | 7/2009 | Ryan et al. | |
| 2009/0287299 A1* | 11/2009 | Tabor | A61F 2/2418 623/1.26 |
| 2010/0268332 A1 | 10/2010 | Tuval et al. | |
| 2011/0015729 A1 | 1/2011 | Jimenez et al. | |
| 2011/0166636 A1 | 7/2011 | Rowe | |
| 2011/0264196 A1 | 10/2011 | Savage et al. | |
| 2011/0301700 A1 | 12/2011 | Fish et al. | |
| 2011/0313515 A1 | 12/2011 | Quadri et al. | |
| 2012/0053681 A1 | 3/2012 | Alkhatib et al. | |
| 2012/0071969 A1* | 3/2012 | Li | A61F 2/2415 623/2.17 |
| 2012/0078356 A1 | 3/2012 | Fish et al. | |
| 2012/0123529 A1* | 5/2012 | Levi | A61F 2/2433 623/2.11 |
| 2013/0023984 A1 | 1/2013 | Conklin | |
| 2013/0150956 A1* | 6/2013 | Yohanan | A61F 2/2412 623/2.14 |
| 2014/0277389 A1 | 9/2014 | Braido et al. | |
| 2015/0018944 A1 | 1/2015 | O'Connell et al. | |
| 2015/0230923 A1* | 8/2015 | Levi | A61F 2/2418 623/2.36 |
| 2016/0296328 A1 | 10/2016 | Tabor et al. | |

FOREIGN PATENT DOCUMENTS

| | | | |
|---|---|---|---|
| WO | 2008150529 A1 | 12/2008 | |
| WO | 2012032187 A1 | 3/2012 | |
| WO | WO-2015126711 A * | 8/2015 | ............. A61F 2/966 |
| WO | WO-2015126711 A1 * | 8/2015 | ........... A61F 2/2409 |

* cited by examiner

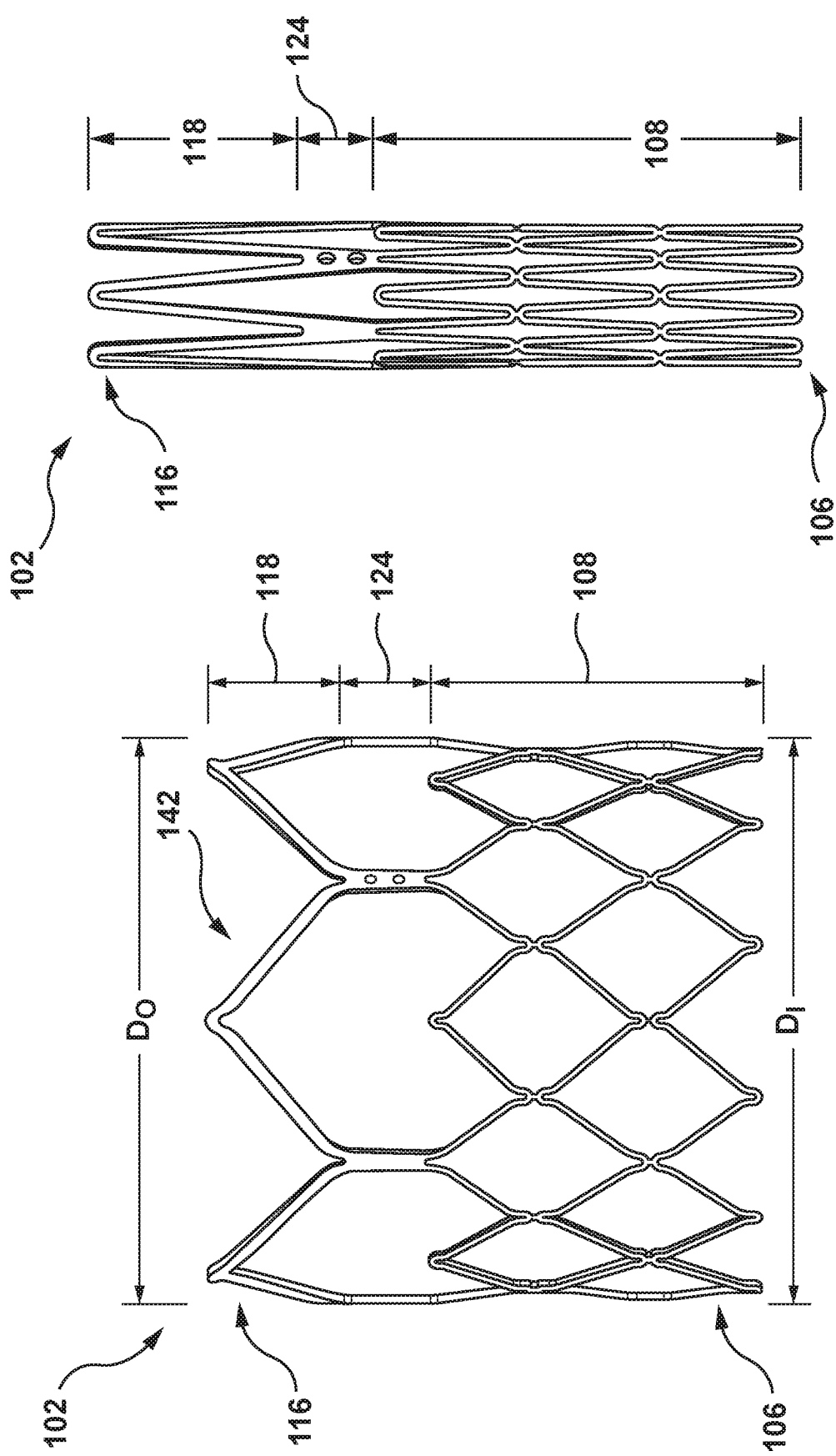

BALLOON EXPANDABLE FRAME FOR TRANSCATHETER IMPLANTATION OF A CARDIAC VALVE PROSTHESIS

CROSS-REFERENCE TO RELATED APPLICATIONS

This application claims the benefit of U.S. Provisional Patent Application Ser. No. 62/801,041, filed Feb. 4, 2019, which is hereby incorporated by reference in its entirety for all purposes. This application also claims the benefit of U.S. Provisional Patent Application Ser. No. 62/880,879, filed Jul. 31, 2019, which is hereby incorporated by reference in its entirety for all purposes.

FIELD OF THE INVENTION

The present invention relates to transcatheter valve prostheses that are radially expandable by a balloon.

BACKGROUND OF THE INVENTION

A human heart includes four heart valves that determine the pathway of blood flow through the heart: the mitral valve, the tricuspid valve, the aortic valve, and the pulmonary valve. The mitral and tricuspid valves are atrioventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Recently, flexible prosthetic valves supported by stent structures that can be delivered percutaneously using a catheter-based delivery system have been developed for heart and venous valve replacement. These prosthetic valves may include either self-expanding or balloon-expandable stent structures with valve leaflets attached to the interior of the stent structure. The prosthetic valve can be reduced in diameter, by crimping onto a balloon catheter or by being contained within a sheath component of a delivery catheter, and advanced through the venous or arterial vasculature. Once the prosthetic valve is positioned at the treatment site, for instance within an incompetent native valve, the stent structure may be expanded to hold the prosthetic valve firmly in place.

When designing a prosthetic valve, valve-frame integration and frame mechanical performance often have competing needs or requirements. For example, when attaching the valve to the frame during valve-frame integration, the valve itself needs to be reinforced to the frame at certain locations without hindering mechanical performance of the frame. Embodiments hereof relate to an improved balloon-expandable transcatheter valve prosthesis configured to minimize tradeoffs between the above-described competing needs.

BRIEF SUMMARY OF THE INVENTION

Embodiments hereof relate to a transcatheter valve prosthesis including a stent and a prosthetic valve. The stent has a crimped configuration for delivery within a vasculature and an expanded configuration for deployment within a native heart valve. The stent is balloon expandable. The stent includes an inflow portion, an outflow portion, and a transition portion extending between the inflow portion and the outflow portion. The inflow portion is formed proximate to an inflow end of the stent, the inflow portion including a plurality of crowns and a plurality of struts with each crown being formed between a pair of opposing struts. A plurality of side openings are defined by the plurality of crowns and the plurality of struts. Endmost inflow side openings and endmost inflow crowns are formed at the inflow end of the stent and the inflow end of the stent has a total of twelve endmost inflow crowns. The outflow portion is formed proximate to an outflow end of the stent, the outflow portion including a plurality of crowns and a plurality of struts with each crown being formed between a pair of opposing struts. Endmost outflow crowns are formed at the outflow end of the stent and the outflow end of the stent has a total of six endmost outflow crowns. A diameter of the inflow end of the stent is the same as a diameter of the outflow end of the stent. The prosthetic valve is disposed within and secured to at least the transition portion of the stent. The prosthetic valve is configured to block blood flow in one direction to regulate blood flow through a central lumen of the stent.

Embodiments hereto also relate to a transcatheter valve prosthesis including a stent, the stent having a crimped configuration for delivery within a vasculature and an expanded configuration for deployment within a native heart valve. The stent is balloon expandable. The stent includes a plurality of axial frame members, an inflow portion including at least three rows of struts and crowns formed between adjacent pairs of said struts, and an outflow portion including a single row of struts and crowns formed between adjacent pair of said struts. The at least three rows of the inflow portion are formed between an inflow end of the axial frame members and an inflow end of the stent. The outflow portion is coupled to an outflow end of the axial frame members. Exactly two struts of the plurality of struts of the outflow portion are disposed between adjacent axial frame members.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 4 is a perspective view of the stent of the transcatheter valve prosthesis of FIG. 1, wherein the stent is in the expanded configuration.

FIG. 5 is a side view of the stent of the transcatheter valve prosthesis of FIG. 1, wherein the stent is in a non-expanded or crimped configuration.

DETAILED DESCRIPTION OF THE INVENTION

Specific embodiments of the present invention are now described with reference to the figures, wherein like reference numbers indicate identical or functionally similar elements. The terms "distal" and "proximal", when used in the following description to refer to a native vessel, native valve, or a device to be implanted into a native vessel or native valve, such as a heart valve prosthesis, are with reference to the direction of blood flow. Thus, "distal" and "distally" refer to positions in a downstream direction with respect to the direction of blood flow and the terms "proximal" and "proximally" refer to positions in an upstream direction with respect to the direction of blood flow.

The following detailed description is merely exemplary in nature and is not intended to limit the invention or the application and uses of the invention. Although the description of the invention is in the context of treatment of an aortic heart valve, the invention may also be used where it is deemed useful in other valved intraluminal sites that are not in the heart. For example, the present invention may be applied to other heart valves or venous valves as well. Furthermore, there is no intention to be bound by any expressed or implied theory presented in the preceding technical field, background, brief summary or the following detailed description.

Figure 1:
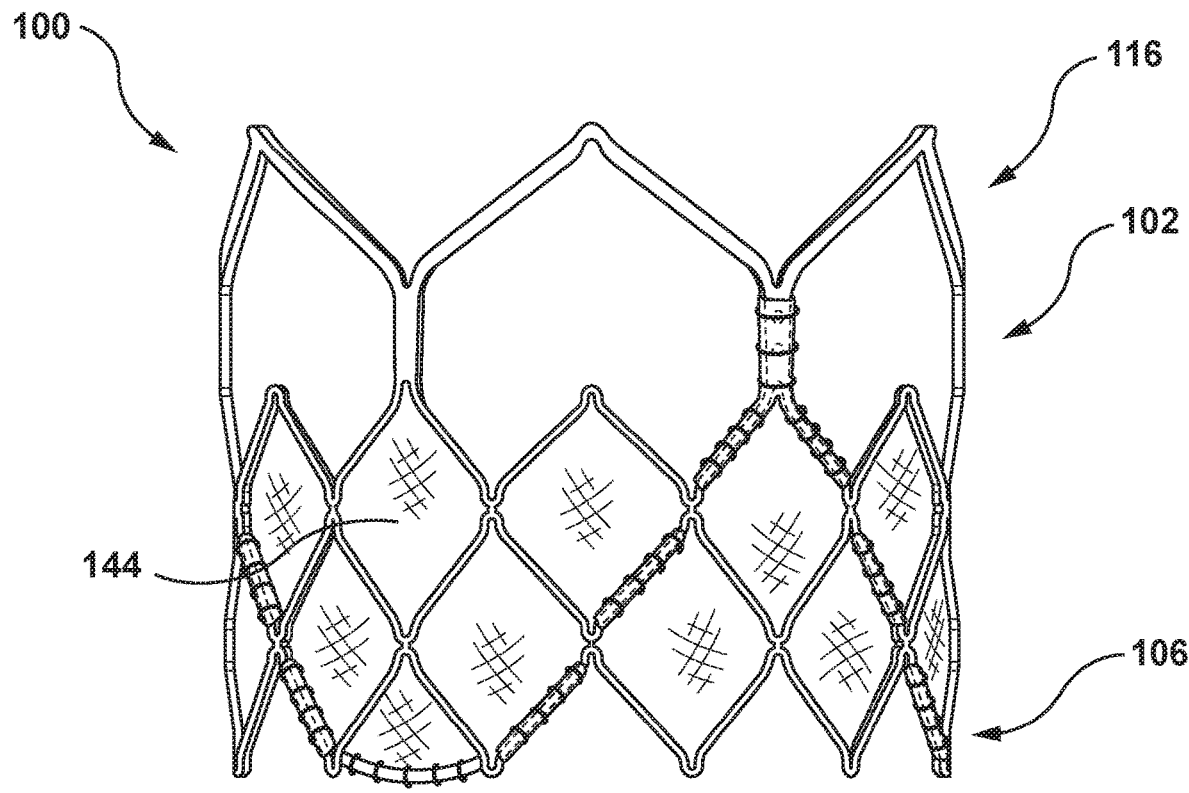
FIG. 1 is a side view of a transcatheter valve prosthesis according to an embodiment hereof, wherein the transcatheter valve prosthesis is in an expanded configuration.
Figure 1A:
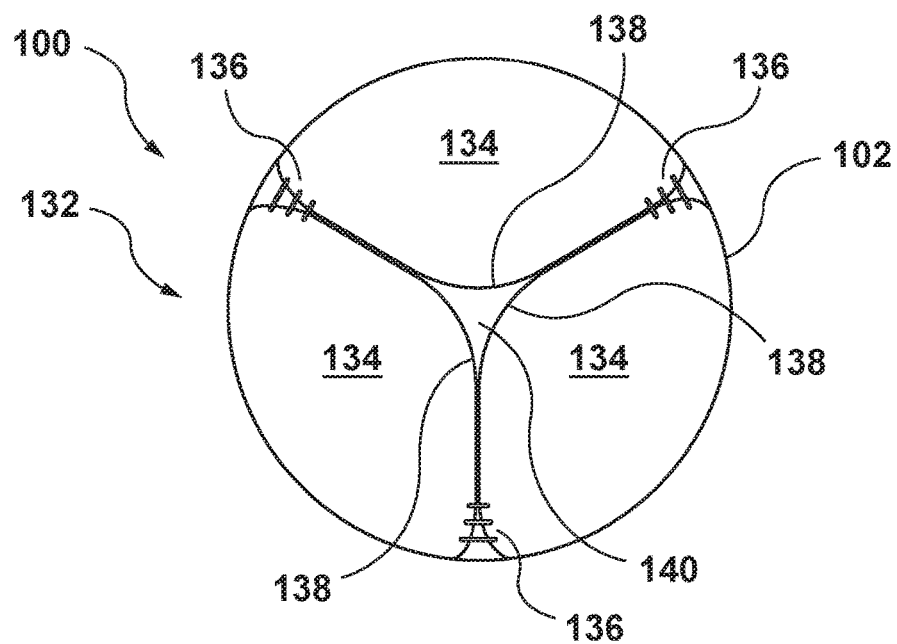
FIG. 1A is an end view illustration of the transcatheter valve prosthesis of FIG. 1.

Embodiments hereof relate to a transcatheter valve prosthesis 100 having a radially-expandable stent 102 and a prosthetic valve 132. The stent 102 is generally tubular, and is mechanically or balloon expandable, having a crimped configuration for delivery within a vasculature and an expanded configuration for deployment within a native heart valve. FIG. 1 is a side view of the transcatheter valve prosthesis 100 in the expanded configuration, while FIG. 1A is an end view illustration of the transcatheter valve prosthesis 100. When the transcatheter valve prosthesis 100 is deployed within the valve annulus of a native heart valve, the stent 102 of the transcatheter valve prosthesis 100 is configured to be radially expanded within native valve leaflets of the patient's defective valve, to thereby retain the native valve leaflets in a permanently open state. In embodiments hereof, the transcatheter valve prosthesis 100 is configured for replacement for an aortic valve such that an inflow end 106 of the transcatheter valve prosthesis 100 extends into and anchors within the aortic annulus of a patient's left ventricle, while an outflow end 116 of the transcatheter valve prosthesis 100 is positioned within the aortic sinuses.

The stent 102 of the transcatheter valve prosthesis 100 may be a unitary frame or scaffold that supports the prosthetic valve 132 including one or more valve leaflets 134 within the interior of the stent 102. The prosthetic valve 132 is capable of blocking flow in one direction to regulate flow there-through via the valve leaflets 134 that may form a bicuspid or tricuspid replacement valve. FIG. 1A is an end view of FIG. 1 taken from the outflow end 116 of the prosthesis and illustrates an exemplary tricuspid valve having three valve leaflets 134, although a bicuspid leaflet configuration may alternatively be used in embodiments hereof. More particularly, as the transcatheter valve prosthesis 100 is configured for placement within a native aortic valve having three leaflets, the prosthetic valve 132 may include three valve leaflets 134. However, the transcatheter valve prosthesis 100 is not required to have the same number of leaflets as the native valve. If the transcatheter valve prosthesis 100 is alternatively configured for placement within a native valve having two leaflets such as the mitral valve, the prosthetic valve 132 may include two or three valve leaflets. The valve leaflets 134 may be attached to a graft material 144 which encloses or lines a portion of the stent 102 as would be known to one of ordinary skill in the art of prosthetic tissue valve construction. The valve leaflets 134 are sutured or otherwise securely and sealingly attached along their bases to the interior surface of the graft material 144, or otherwise attached to the stent 102. Adjoining pairs of leaflets are attached to one another at their lateral ends to form commissures 136, with free edges 138 of the valve leaflets 134 forming coaptation edges that meet in area of coaptation 140.

The valve leaflets 134 may be made of pericardial material; however, the valve leaflets 134 may instead be made of another material. Natural tissue for the valve leaflets 134 may be obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals. Synthetic materials suitable for use as the valve leaflets 134 include DACRON® polyester commercially available from Invista North America S.A.R.L. of Wilmington, Del., other cloth materials, nylon blends, polymeric materials, and vacuum deposition nitinol fabricated materials. One polymeric material from which the leaflets can be made is an ultra-high molecular weight polyethylene material commercially available under the trade designation DYNEEMA from Royal DSM of the Netherlands. With certain leaflet materials, it may be desirable to coat one or both sides of the leaflet with a material that will prevent or minimize overgrowth. It is further desirable that the leaflet material is durable and not subject to stretching, deforming, or fatigue.

Graft material 144 may enclose or line the stent 102 as would be known to one of ordinary skill in the art of prosthetic tissue valve construction. Graft material 144 may be a natural or biological material such as pericardium or another membranous tissue such as intestinal submucosa. Alternatively, graft material 144 may be a low-porosity woven fabric, such as polyester, Dacron fabric, or PTFE, which creates a one-way fluid passage when attached to the stent. In one embodiment, graft material 144 may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example.

As previously stated, the stent 102 is balloon-expandable as would be understood by one of ordinary skill in the art. As such, the stent 102 is made from a plastically deformable material such that when expanded by a dilatation balloon, the stent 102 maintains its radially expanded configuration. The stent 102 may be formed from stainless steel or other suitable metal, such as platinum iridium, cobalt chromium alloys such as MP35N, or various types of polymers or other materials known to those skilled in the art, including said materials coated with various surface deposits to improve clinical functionality. The stent 102 is configured to be rigid such that it does not deflect or move when subjected to in-vivo forces, or such that deflection or movement is minimized when subjected to in-vivo forces. In an embodiment, the radial stiffness (i.e., a measurement of how much the stent 102 deflects when subjected to in-vivo forces) of the stent 102 is between 80 N/m and 120 N/m, and the radial stiffness of the stent 102 scaled across the deployed height thereof is approximately 5 N/mm$^2$. In an embodiment, the radial stiffness of the stent 102 is greater than 100 N/m. Further, in an embodiment, the device recoil (i.e., a measurement of how much the stent 102 relaxes after balloon deployment) is below 15% and the approximately recoil after deployment is between 1 mm and 2 mm. Further, in an embodiment, the device crush or yield (i.e., the radial force at which the stent 102 yields) is approximately 200 N.

Delivery of the transcatheter valve prosthesis 100 may be accomplished via a percutaneous transfemoral approach or a transapical approach directly through the apex of the heart via a thoracotomy, or may be positioned within the desired area of the heart via different delivery methods known in the art for accessing heart valves. The transcatheter valve prosthesis 100 has a crossing profile of between 15-30 Fr, the crossing profile being defined as the outside diameter (OD) of the transcatheter valve prosthesis 100 after it is crimped onto the balloon and allowed to recoil from the crimping action. During delivery, the transcatheter valve prosthesis 100 remains compressed until it reaches a target diseased native heart valve, at which time a balloon of a balloon catheter is inflated in order to radially expand the transcatheter valve prosthesis 100 in situ. The balloon catheter is then removed and the transcatheter valve prosthesis 100 remains deployed within the native target heart valve.

Figure 3:
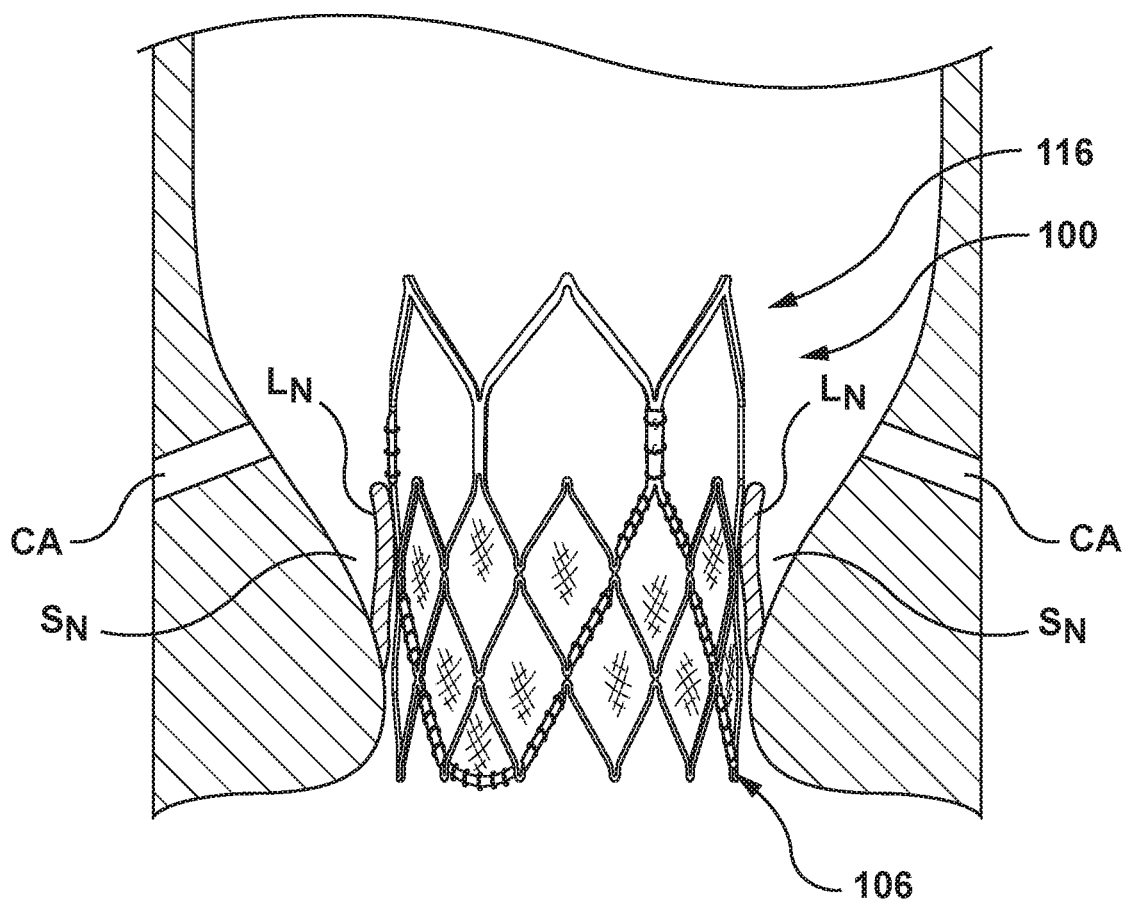
FIG. 3 is a side view illustration of the transcatheter valve prosthesis of FIG. 1 implanted within a native aortic valve annulus.

FIG. 3 illustrates the transcatheter valve prosthesis 100 implanted in situ within a native aortic valve annulus, which is shown in section, having native leaflets $L_N$ and corresponding native sinuses $S_N$. FIG. 3 also illustrates placement of the coronary arteries CA. The transcatheter valve prosthesis 100 is configured for intra-annular placement within a native aortic valve. More particularly, the inflow end 106 of the transcatheter valve prosthesis 100 extends into and anchors within the aortic annulus of a patient's left ventricle, while the outflow end 116 of the transcatheter valve prosthesis 100 is positioned within the aortic sinuses, with no portion of the transcatheter valve prosthesis 100 extending into the patient's ascending aorta. When the transcatheter valve prosthesis 100 is deployed within the valve annulus of a native heart valve, the stent 102 is configured to be expanded within native valve leaflets $L_N$ of the patient's defective valve, to thereby retain the native valve leaflets in a permanently open state. A height or length of the stent 102 in the expanded configuration is between 12 and 24 mm, the height being measured from the most proximal part thereof (endmost inflow crowns 110A, which will be described in more detail herein) to the most distal part thereof (endmost outflow crowns 120A, which will be described in more detail herein). In an embodiment hereof, a height or length of the stent 102 in the expanded configuration is between 18 and 24 mm. For example, in an embodiment the stent 102 has diameter of between 21-24 mm and a height of 19 mm. In another embodiment, the stent 102 has diameter of between 24-27 mm and a height of 21 mm. In yet another embodiment, the stent 102 has diameter of between 27-30 mm and a height of 23 mm.

Figure 6:
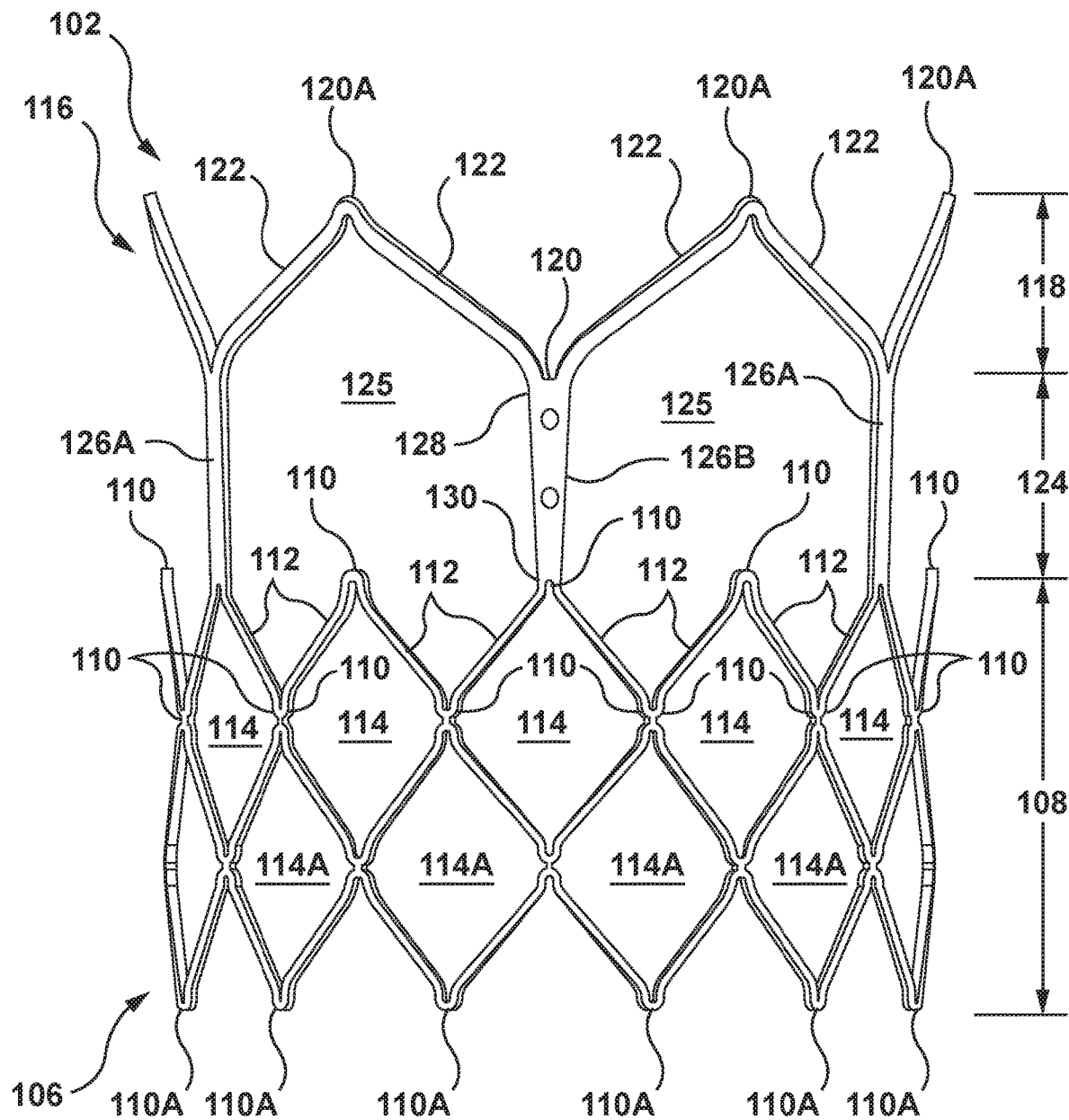
FIG. 6 is a side view of the stent of the transcatheter valve prosthesis of FIG. 1, wherein the stent is in the expanded configuration.
Figure 7:
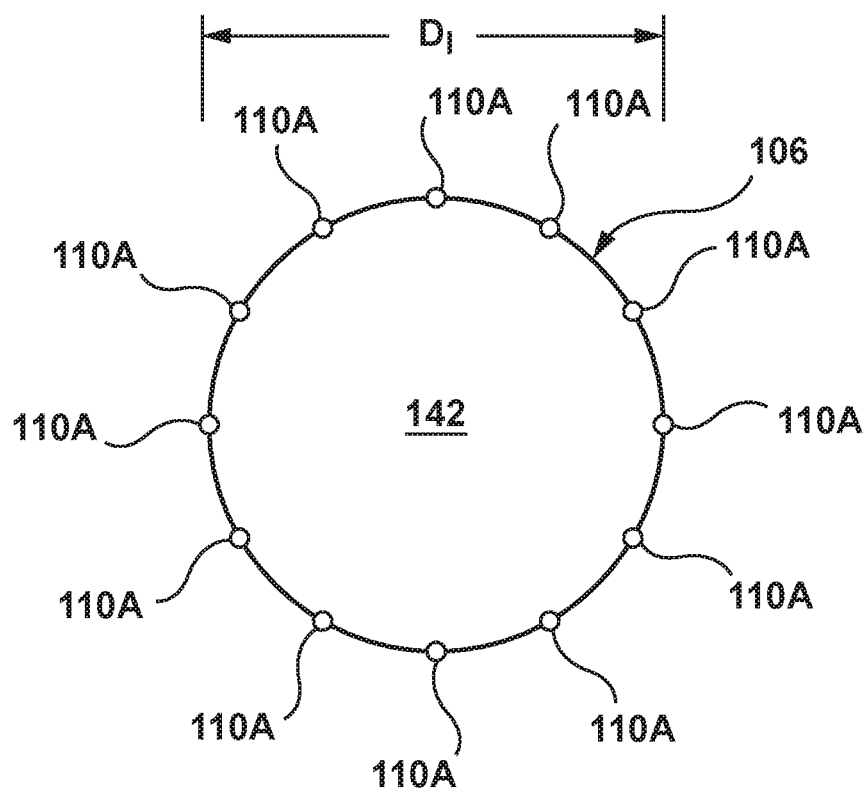
FIG. 7 is an end view of an inflow end of the stent of the transcatheter valve prosthesis of FIG. 1.
Figure 8:
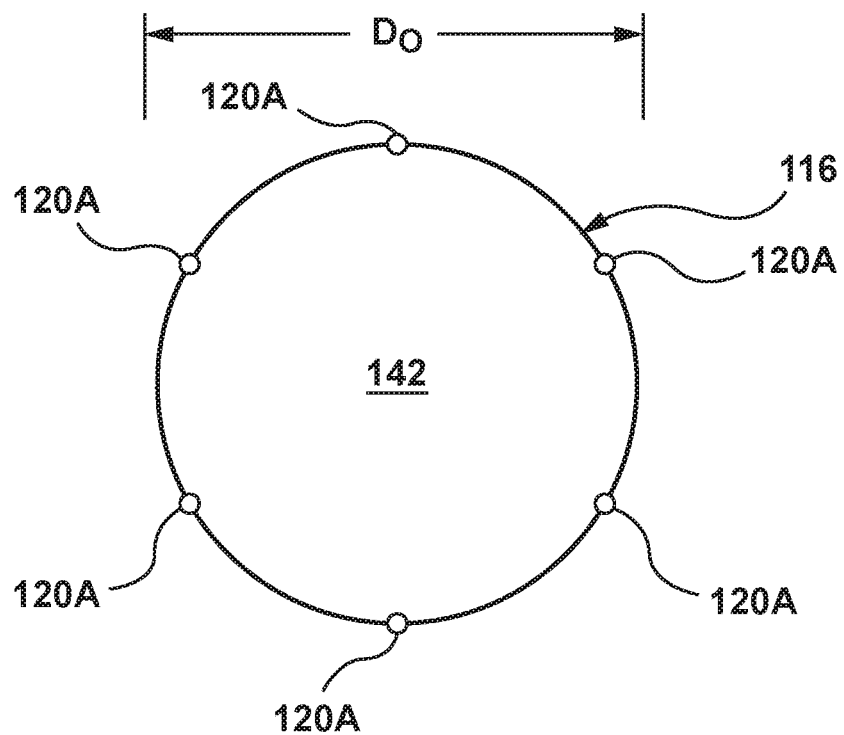
FIG. 8 is an end view of an outflow end of the stent of the transcatheter valve prosthesis of FIG. 1.

The stent 102 will now be described in more detail. The stent 102 includes an inflow portion 108, an outflow portion 118, and a transition portion 124 bridging, connecting, or otherwise extending between the inflow portion 108 and the outflow portion 118. The stent 102 is a tubular component defining a central lumen or passageway 142, and further defines the inflow or proximal end 106 and the outflow or distal end 116 of the transcatheter valve prosthesis 100. When expanded, a diameter $D_I$ of the inflow end 106 of the stent 102 is the same as a diameter $D_O$ of the outflow end 116 of the stent 102. In an embodiment, the diameters $D_I$ and $D_O$ may range between 18 and 30 mm in order to accommodate dimensions of the native valve anatomy. Stated another way, it may be desirable for the transcatheter valve prosthesis 100 to be available in varying size increments to accommodate varying diameters or sizes of a patient's native annulus. The stent 102 may be formed by a laser-cut manufacturing method and/or another conventional stent forming method as would be understood by one of ordinary skill in the art. The cross-section of the stent 102 may be circular, ellipsoidal, rectangular, hexagonal, square, or other polygonal shape, although at present it is believed that circular or ellipsoidal may be preferable with the transcatheter valve prosthesis 100 being provided for replacement of an aortic valve. The stent 102 has an expanded configuration, which is shown in the perspective and side views of FIGS. 4 and 6, respectively, and a non-expanded or crimped configuration, which is shown in the side view of FIG. 5. Non-expanded or crimped configuration as used herein refers to the configuration of the stent 102 after crimping onto a balloon of a balloon catheter for delivery. FIG. 7 is an end view of the inflow end 106 of the stent 102, while FIG. 8 is an end view of the outflow end 116 of the stent 102.

Figure 6A:
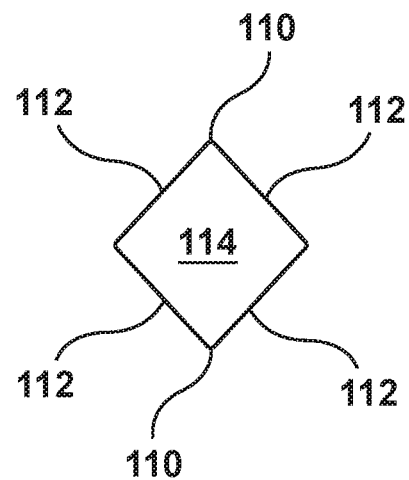
FIG. 6A is an enlarged side view of a single cell or side opening of an inflow portion of the stent of the transcatheter valve prosthesis of FIG. 1, wherein the stent is in the expanded configuration.

The inflow portion 108 is formed proximate to the inflow end 106 of the stent. The inflow portion 108 includes a plurality of crowns 110 and a plurality of struts 112 with each crown 110 being formed between a pair of opposing struts 112. Each crown 110 is a curved segment or bend extending between opposing struts 112. The inflow portion 108 is tubular, with a plurality of side openings 114 being defined by the plurality of crowns 110 and the plurality of struts 112. In an embodiment, the plurality of side openings 114 may be diamond-shaped. More particularly, as best shown in FIG. 6A which is a side view of a single side opening 114 of the inflow portion 108 of the stent 102, each side opening 114 is formed by two pairs of opposing crowns 110 and four struts 112 therebetween. Each side opening 114 is symmetrical for easier integration with the prosthetic valve 132. A series of endmost inflow side openings 114A and a series of endmost inflow crowns 110A are formed at the inflow end 106 of the stent 102. The inflow end 106 of the stent 102 has a total of twelve endmost inflow crowns 110A, as best shown in the end view of FIG. 7.

Figure 2:
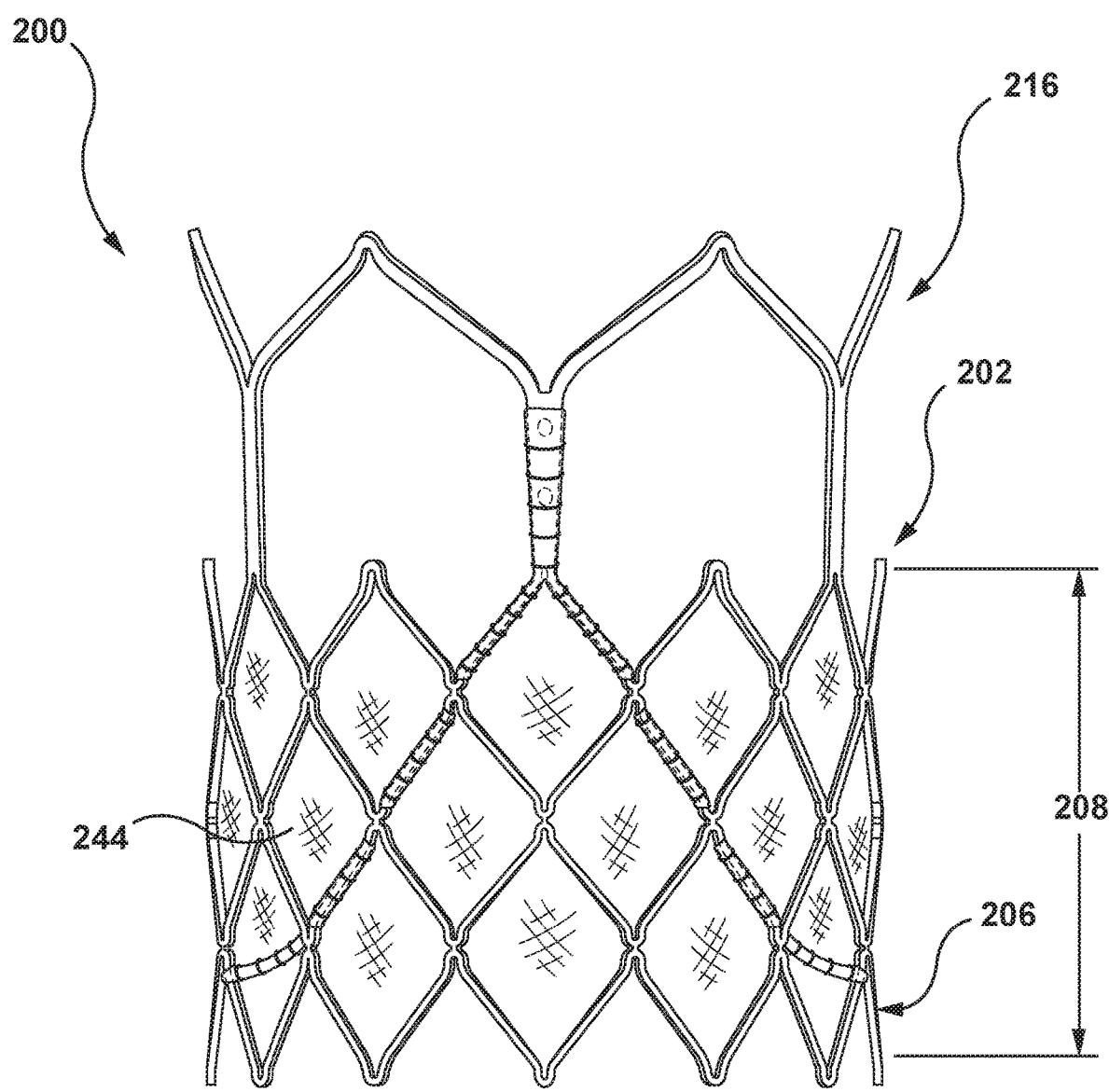
FIG. 2 is a side view of a transcatheter valve prosthesis according to another embodiment hereof, wherein the transcatheter valve prosthesis is relatively longer and shown in an expanded configuration.

The length or height of the inflow portion 108 may vary from that depicted herein in order to accommodate dimensions of the native valve anatomy. For example, in another embodiment hereof as shown in FIG. 2, a transcatheter valve prosthesis 200 is shown that is relatively longer than the transcatheter valve prosthesis 100. More particularly, the transcatheter valve prosthesis 200 includes a stent 202 having graft material 244 which encloses or lines a portion of the stent 202 as would be known to one of ordinary skill in the art of prosthetic tissue valve construction. The stent 202 is a tubular component that defines an inflow end 206 and an outflow end 216 of the transcatheter valve prosthesis 200. An inflow portion 208 of the stent 202 is relatively longer than the inflow portion 108 of the stent 108 so that the overall length or height of the transcatheter valve prosthesis 200 may be relatively increased to accommodate dimensions of the native valve anatomy. For example, a height or length of the stent 202 in the expanded configuration is between 18-24 mm.

The outflow portion 118 is formed proximate to the outflow end 116 of the stent. The outflow portion 118 includes a plurality of crowns 120 and a plurality of struts 122 with each crown 120 being formed between a pair of opposing struts 122. Each crown 120 is a curved segment or bend extending between opposing struts 122. The inflow portion 108 is a ring. A series of endmost outflow crowns 120A are formed at the outflow end 116 of the stent 102. The outflow end 116 of the stent 102 has a total of six endmost outflow crowns 120A, as best shown in the end view of FIG. 8. In this embodiment, the endmost outflow crowns 120A of are not connected to axial frame members 126 of the transition portion 124 but rather may be considered to be free or unattached while the remaining outflow crowns 120 of the outflow portion 118 are connected to the axial frame members 126 and disposed closer to the inflow end 106 than the endmost outflow crowns 120A.

The transition portion 124 bridges, connects, or otherwise extends between the inflow portion 108 and the outflow portion 118. The transition portion 124 includes a total of six axial frame members 126, each axial frame member 126 extending between a crown 120 of the outflow portion 118 and a crown 110 of the inflow portion 108. More particularly, each axial frame member 126 is an axial segment having a first end 128 connected to a crown 120 of the outflow portion 118 and a second end 130 connected to a crown 110 of the inflow portion 108. The axial frame members 126 are substantially parallel to the central longitudinal axis of the stent 102. Each axial frame member 126 is disposed approximately halfway between a pair of adjacent endmost outflow crowns 120A. Three of the six axial frame members 126 are commissure posts 126A and aligned with and attached to a respective commissure of the three leaflets 134 of the prosthetic valve 132. Three of the axial frame members 126 are axial struts 126B and are disposed between adjacent commissure posts 126A. The axial frame members 126 aid in valve alignment and coaptation. More particularly, the axial frame members 126 reinforce or strengthen the commissure region of the prosthetic valve 132 by shaping the leaflets 134 and supporting the leaflets 134 during opening and closing thereof, and thus provide more reliable leaflet coaptation. Symmetrical cell expansion ensures that the stent 102 crimps well onto a balloon of a balloon catheter for delivery. Poor crimp quality may lead to portions of the stent overlapping when crimped, which in turn may cause tissue damage to the valve leaflets of the prosthetic valve during the crimping process.

The prosthetic valve 132 is disposed within and secured to at least the transition portion 124 of the stent 102 at the commissure posts 126. In addition, the prosthetic valve 132 may also be disposed within and secured to the inflow portion 108 of the stent 102.

Figure 6B:
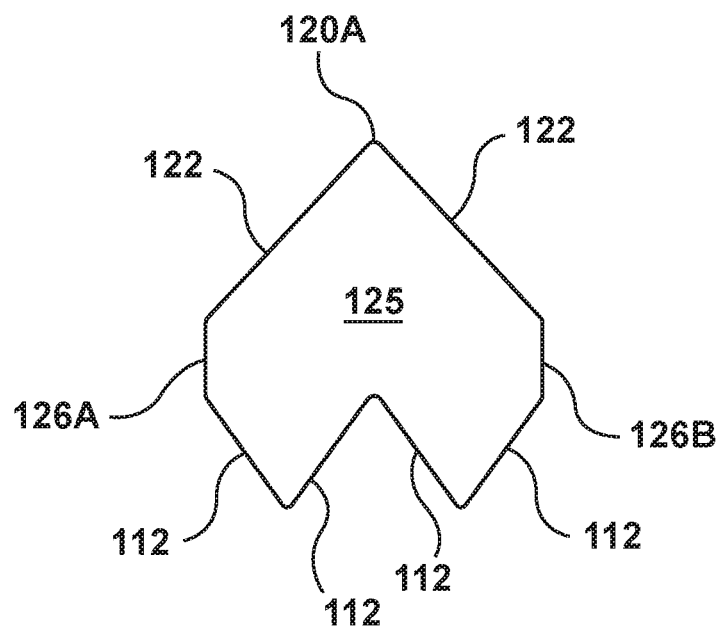
FIG. 6B is an enlarged side view of a single endmost opening of the stent of the transcatheter valve prosthesis of FIG. 1, wherein the stent is in the expanded configuration.

In the embodiment shown, there is a single row of struts 122 and crowns 120 between the first ends 128 and the outflow end 116 of the stent 102. Further, in the embodiment shown, exactly two struts 122 and a single crown 120 of the outflow portion 118 are disposed between adjacent axial frame members 126. Such an arrangement provides a series of six endmost outflow side openings 125 formed at the outflow portion 118 of the stent 102. Each endmost outflow side opening 125 is heart-shaped. More particularly, as best shown in FIG. 6B which is a side view of a single endmost outflow side opening 125 of the stent 102, each endmost outflow side opening 125 is defined by two adjacent struts 122 of the outflow portion 118, four adjacent struts 112 of the inflow portion 108, and two adjacent axial frame members 126 of the transition portion 124. The endmost outflow side openings 125 of the outflow portion 118 are relatively larger than the plurality of side openings 114 of the inflow portion 108 (defined by four adjacent struts 112 of the inflow portion 108) to improve access to the coronary arteries. More particularly, the endmost outflow side openings 125 of the outflow portion 118 are configured to be of sufficient size to be easily crossed with a coronary guide catheter into either the right coronary artery or the left main coronary artery once the transcatheter valve prosthesis 100 is deployed in situ. The inflow portion 108 includes exactly three rows of struts 112 and crowns 110 between the second ends 130 of the commissure bars 126 and the inflow end 106 of the stent 102. Further, four struts 112 and three crowns 110 are disposed between the second ends 130 of adjacent commissure bars 126.

Figure 9:
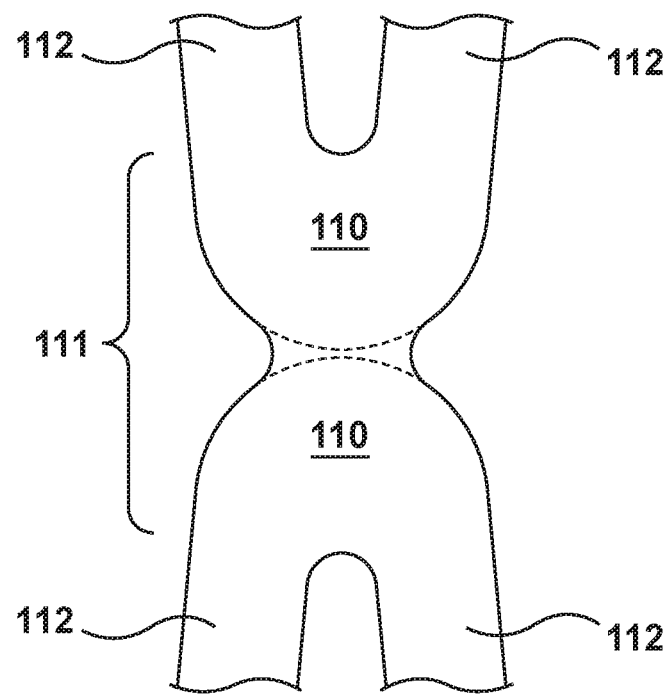
FIG. 9 is an enlarged side view of a node of an inflow portion of the stent of the transcatheter valve prosthesis of FIG. 1.
Figure 10:
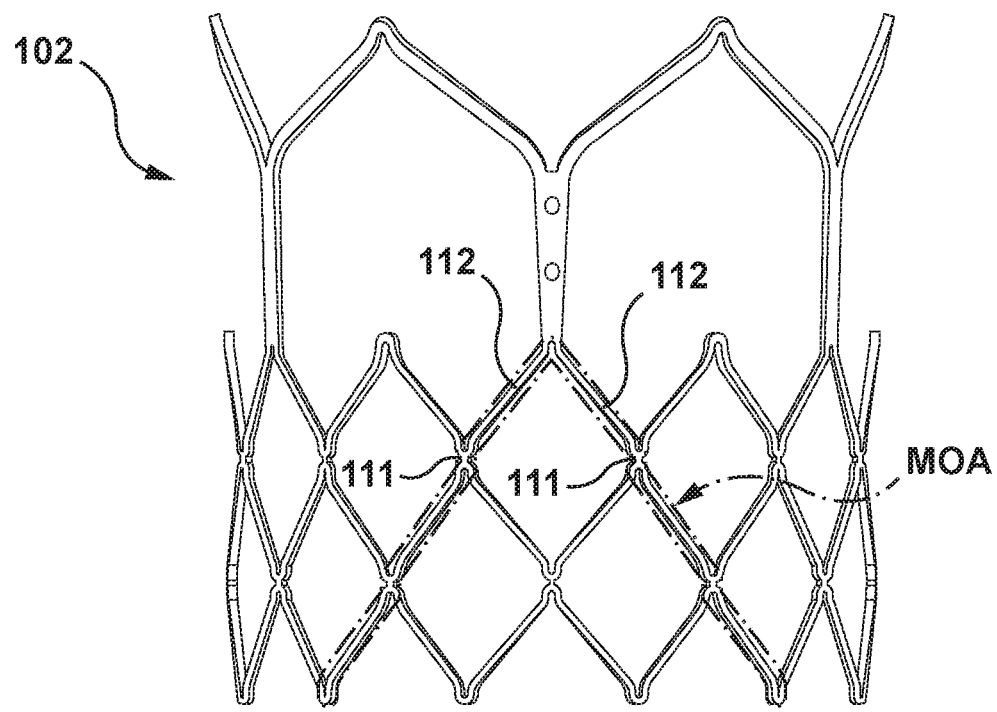
FIG. 10 is a side view of the stent including the nodes of FIG. 9, wherein the stent is in the expanded configuration and a margin of attachment is shown thereon for illustrative purposes only.

The three leaflets 134 of the prosthetic valve 132 are attached to the stent 102 along a margin of attachment that follows struts 112 and nodes 111 of the inflow portion 108 of the stent 102. With the margin of attachment following the frame structure, the prosthetic valve 132 is more fully secured to the stent 102 and minimizes suture or tissue tearing from the stent 102 during operation. With reference to FIGS. 9 and 10, a node 111 is defined as a region where two crowns of the plurality of crowns 110 within the inflow portion 108 connect. In the embodiment of FIG. 9, which is an enlarged side view of a node 111 within the inflow portion 108 of the stent 102, two crowns 110 abut against each other without any overlap of the bends thereof. The bends of the two crowns 110 are shown in phantom for illustrative purposes only. FIG. 10 is a side view of the stent 102 including the nodes 111 of FIG. 9, and a margin of attachment MOA is shown thereon for illustrative purposes only. As shown in FIG. 10, the margin of attachment MOA follows the struts 112 as well as the nodes 111. The margin of attachment MOA extends vertically along the nodes 111 and is angled along the struts 112. Thus, in this embodiment, the margin of attachment MOA has a generally concave shape but includes a plurality of vertical steps along the nodes 111 of the stent 102.

Figure 11:
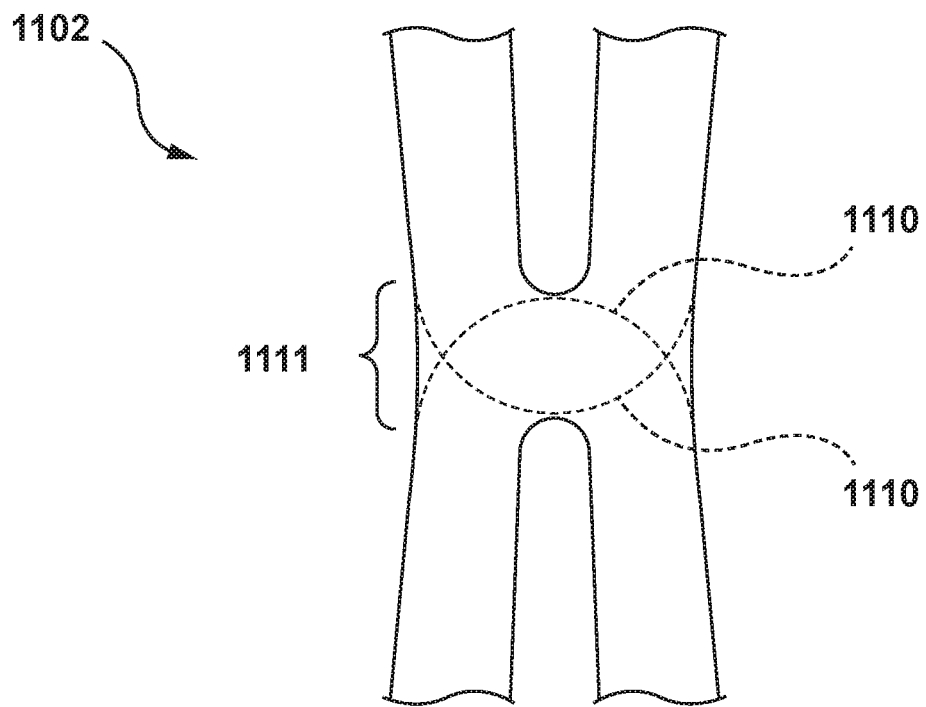
FIG. 11 is an enlarged side view of a node according to another embodiment hereof.
Figure 12:
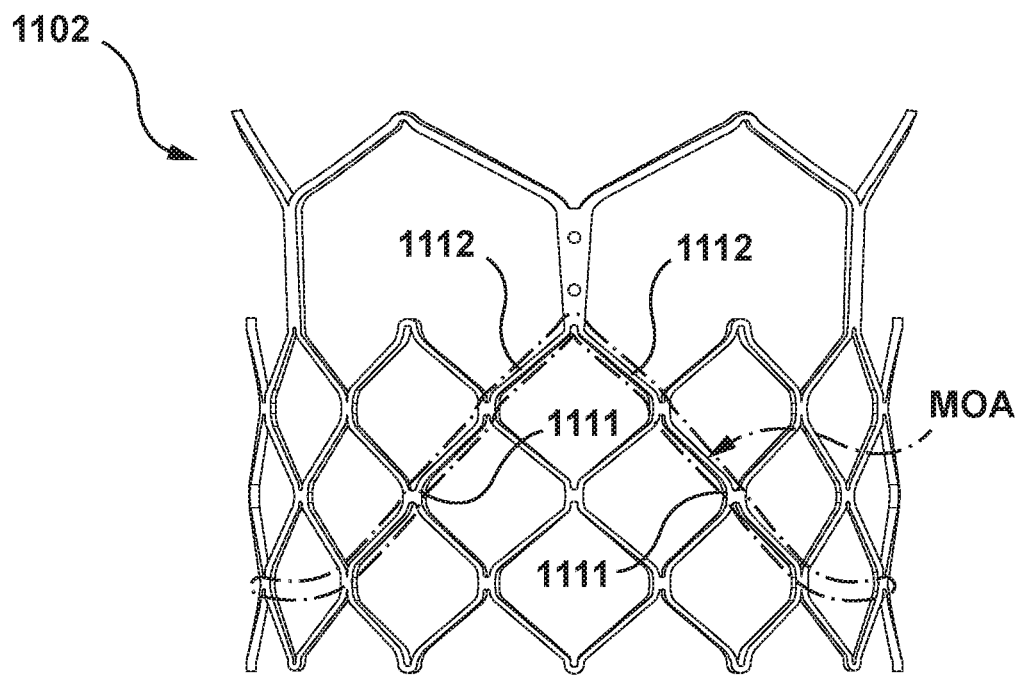
FIG. 12 is a side view of a stent including the nodes of FIG. 11, wherein the stent is in the expanded configuration and a margin of attachment is shown thereon for illustrative purposes only.

In another embodiment shown in FIGS. 11 and 12, a stent 1102 includes a different node configuration that results in a margin of attachment MOA that has a smooth concave shape without the vertical steps described above. More particularly, FIG. 11 is an enlarged side view of a node 1111 according to another embodiment hereof. FIG. 12 is a side view of the stent 1102 including the nodes 1111 of FIG. 11, and a margin of attachment MOA is shown thereon for illustrative purposes only. In the embodiment of FIGS. 11 and 12, two crowns 1110 "overlap" each other such that the nodes 1111 have a relatively reduced height. The bends of the two crowns 1110 are shown in phantom for illustrative purposes only. The node 1111 in which the two crowns 110 overlap each other is relatively shorter or has a relatively reduced height compared to the node 111 in which the two crowns 110 abut against each other. The two crowns 1110 of the node 1111 do not overlap in terms of thickness or layers but rather overlap in terms of geometry. More particularly, the two crowns 1110 overlap in the sense that the bends of the two crowns 1110 overlay or are superimposed over each other. However, the node 1111 has the same thickness as a single crown 1110. This node configuration results in a smoother margin of attachment. As shown in FIG. 12, the margin of attachment MOA follows the struts 1112 as well as the nodes 1111. The margin of attachment MOA curves or is angled along the nodes 1111 and curves or is angled along the struts 1112. Thus, in this embodiment, the margin of attachment MOA has a smooth concave shape that does not include a plurality of vertical steps as described above with respect to FIGS. 9 and 10. The smooth concave shape of the margin of attachment MOA maximizes valve performance, because such valve attachment improves leaflet durability and hemodynamics of the prosthetic valve (not shown). As will be understood by one of ordinary skill in the art, FIG. 12 illustrates the stent 1102 having a relatively longer inflow portion similar to the inflow portion 208 described above with respect to FIG. 2, but nodes 1111 may be utilized on any inflow portion and any stent described herein.

Figure 13:
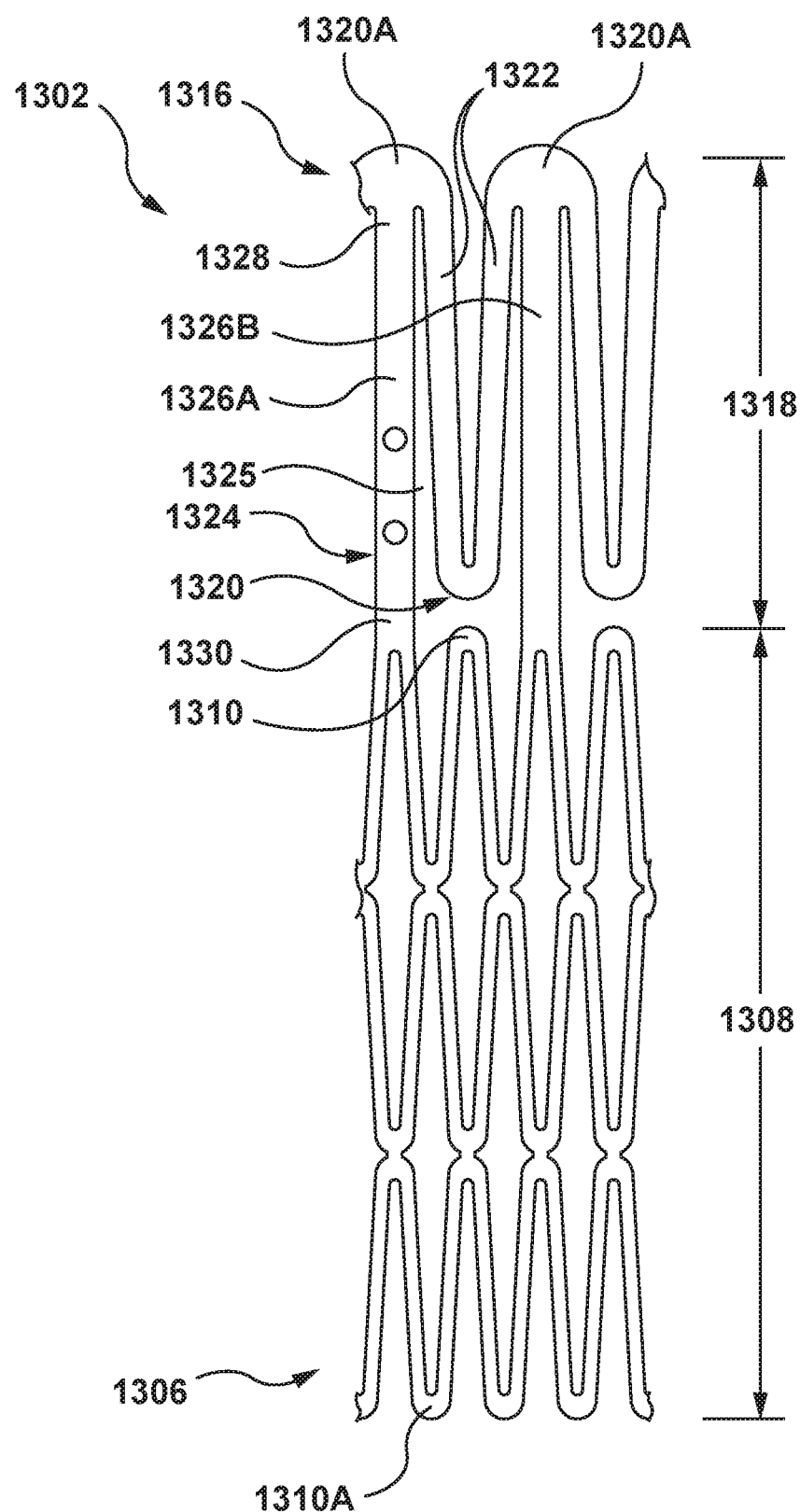
FIG. 13 is a side view of a stent according to another embodiment hereof, wherein the stent is in a non-expanded or crimped configuration and crowns of an outflow portion of the stent are inverted.

FIG. 13 is a side view of a stent 1302 according to another embodiment hereof. In FIG. 13, the stent 1302 is in a non-expanded or crimped configuration. The stent 1302 is similar to the stent 102 except that the crowns 1320 of an outflow portion 1318 of the stent 1302 are inverted as compared to the crowns 120 of the outflow portion 118 of the stent 102. More particularly, the stent 1302 is balloon-expandable and is includes an inflow portion 1308, an outflow portion 1318, and a transition portion 1324 bridging, connecting, or otherwise extending between the inflow portion 1308 and the outflow portion 1318. The stent 1302 is a tubular component defining a central lumen or passageway (not shown on FIG. 13) and having an inflow or proximal end 1306 and an outflow or distal end 1316. When expanded, a diameter of the inflow end 1306 of the stent 1302 is the same as a diameter of the outflow end 1316 of the stent 1302. The stent 1302 may be formed by a laser-cut manufacturing method and/or another conventional stent forming method as would be understood by one of ordinary skill in the art. The cross-section of the stent 1302 may be circular, ellipsoidal, rectangular, hexagonal, square, or other polygonal shape, although at present it is believed that circular or ellipsoidal may be preferable when utilized with the replacement of an aortic valve. Although FIG. 13 illustrates the stent 1302 in its non-expanded or crimped configuration, it will be understood by one of ordinary skill in the art that the stent 1302 has an expanded configuration.

A prosthetic valve (not shown) is disposed within and secured to at least the transition portion 1324 of the stent 1302. In addition, the prosthetic valve may also be disposed within and secured to the inflow portion 1308 of the stent 1302. The prosthetic valve is the same as prosthetic valve 132 described above. The inflow portion 1308 is formed proximate to the inflow end 1306 of the stent, and is the same as inflow portion 108 described above. The inflow portion 1308 of the stent 1302 may be formed with nodes 111 having abutting crowns 110 as described in FIGS. 9 and 10 above, or may be formed with shortened nodes 1111 having overlapping crowns 1110 as described in FIGS. 11 and 12 above. Similar to the stent 102, the inflow end 1306 of the stent 1302 has a total of twelve endmost inflow crowns 1310A.

The outflow portion 1318 is formed proximate to the outflow end 1316 of the stent 1302. The outflow portion 1318 includes a plurality of crowns 1320 and a plurality of struts 1322 with each crown 1320 being formed between a pair of opposing struts 1322. Each crown 1320 is a curved segment or bend extending between opposing struts 1322. The outflow portion 1318 is a ring. A series of endmost outflow crowns 1320A are formed at the outflow end 1316 of the stent 1302. Similar to the stent 102, the outflow end 1316 of the stent 1302 has a total of six endmost outflow crowns 1320A.

The transition portion 1324 bridges, connects, or otherwise extends between the inflow portion 1308 and the outflow portion 1318. The transition portion 1324 includes a total of six axial frame members 1326, each axial frame member 1326 extending between an endmost outflow crown 1320A of the outflow portion 1318 and a crown 1310 of the inflow portion 1308. More particularly, each axial frame member 1326 is an axial segment having a first end 1328 connected to an endmost outflow crown 1320A of the outflow portion 1318 and a second end 1330 connected to a crown 1310 of the inflow portion 1308. Each axial frame member 1326 is aligned with an endmost outflow crown 1320A. Three of the six axial frame members 1326 are commissure posts 1326A and are aligned with and attached to respective commissures of the three leaflets of the prosthetic valve. Three of the axial frame members 1326 are axial struts 1326B disposed between two of the commissure posts 1326A. The axial frame members 1326 aid in valve alignment and coaptation. More particularly, the axial frame members 1326 reinforce or strengthen the commissure region of the prosthetic valve 1332 by shaping the leaflets and supporting the leaflets during opening and closing thereof, and thus provide more reliable leaflet coaptation.

In the embodiment shown, there is a single row of struts 1322 and crowns 1320 coupled to the first ends 1328 of the axial frame members 1326 and defining the outflow end 1316 of the stent 1302. Further, in the embodiment shown, exactly two struts 1322 and a single crown 1320 of the outflow portion 1318 are disposed between adjacent axial frame members 126. Such an arrangement provides a series of six endmost outflow side openings 1325 formed at the outflow portion 1318 of the stent 1302. Each of the endmost outflow side opening 1325 is defined by two adjacent struts 1322 of the outflow portion 1318, four adjacent struts 1312 of the inflow portion 1308, and two adjacent axial frame members 1326 of the transition portion 1324.

In this embodiment, the endmost outflow crowns 1320A of the outflow portion 1318 are connected to the axial frame members 1326 while the free or unattached crowns 1320 of the outflow portion 1318 are disposed closer to the inflow end 1306 than the endmost outflow crowns 1320A. This configuration allows the length of the axial frame members 1326 to be increased relative to the axial frame members 126 of the stent 102 to maximize space for valve attachment.

As with the stent 102, the inflow portion 1308 includes exactly three rows of struts 1312 and crowns 1310 between the second ends 1330 of the axial frame members 1326 and the inflow end 1306 of the stent 1302. Further, four struts 1312 and three crowns 1310 are disposed between the second ends 1330 of adjacent axial frame members 1326.

Figure 14:
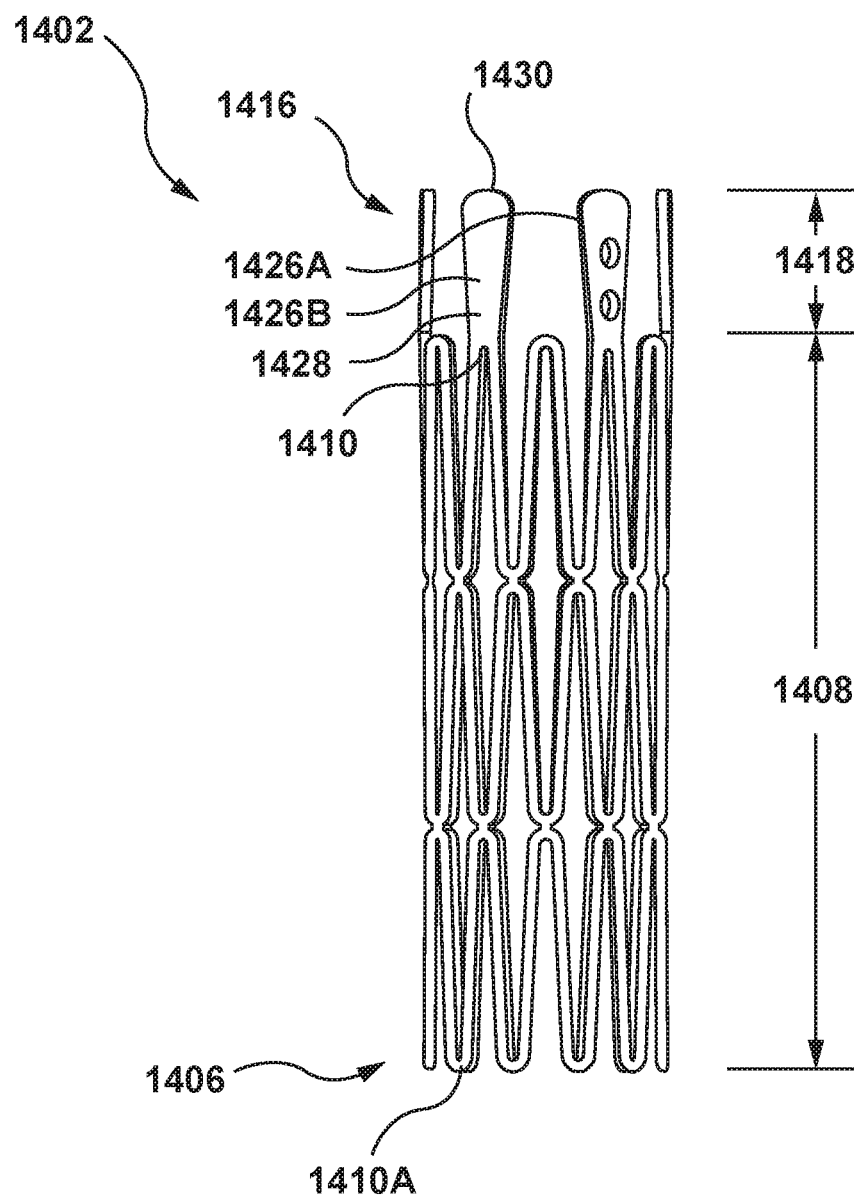
FIG. 14 is a side view of a stent according to another embodiment hereof, wherein the stent is in an expanded configuration and an outflow portion of the stent does not include crowns.

FIG. 14 is a side view of a stent 1402 according to another embodiment hereof. In FIG. 14, the stent 1402 is in a non-expanded or crimped configuration. An outflow portion 1418 of a stent 1402 does not include crowns. More particularly, the stent 1402 is balloon-expandable and includes an inflow portion 1408 and the outflow portion 1418. The stent 1402 is a tubular component defining a central lumen or passageway (not shown on FIG. 14) and having an inflow or proximal end 1406 and an outflow or distal end 1416. When expanded, a diameter of the inflow end 1406 of the stent 1402 is the same as a diameter of the outflow end 1416 of the stent 1402. The stent 1402 may be formed by a laser-cut manufacturing method and/or another conventional stent forming method as would be understood by one of ordinary skill in the art. The cross-section of the stent 1402 may be circular, ellipsoidal, rectangular, hexagonal, square, or other polygonal shape, although at present it is believed that circular or ellipsoidal may be preferable when utilized with the replacement of an aortic valve. Although FIG. 14 illustrates the stent 1402 in its non-expanded or crimped configuration, it will be understood by one of ordinary skill in the art that the stent 1402 has an expanded configuration.

A prosthetic valve (not shown) is disposed within and secured to at least the outflow portion 1418 of the stent 1402. In addition, the prosthetic valve may also be disposed within and secured to the inflow portion 1408 of the stent 1402. The prosthetic valve is the same as prosthetic valve 132 described above. The inflow portion 1408 is formed proximate to the inflow end 1406 of the stent, and is the same as inflow portion 108 described above. The inflow portion 1408 of the stent 1402 may be formed with nodes 111 having abutting crowns 110 as described in FIGS. 9 and 10 above, or may be formed with shortened nodes 1111 having overlapping crowns 1110 as described in FIGS. 11 and 12 above. Similar to the stent 102, the inflow end 1406 of the stent 1402 has a total of twelve endmost inflow crowns 1410A.

The outflow portion 1418 is formed proximate to the outflow end 1416 of the stent 1402. The outflow portion 1418 includes a minimum of three axial frame members 1426. In an embodiment, the outflow portion 1418 includes up to six axial frame members 1426, with three of the axial frame members 1426 being commissure posts 1426A. Each axial frame members 1426 longitudinally extends from a crown 1410 of the inflow portion 1408. More particularly, each axial frame members 1426 is a relatively stiff, axial segment having a first end 1428 connected to a crown 1410 of the inflow portion 1408 and an unattached or free second end 1430. Three of the axial frame members 1426 are commissure posts 1426A circumferentially spaced apart and aligned with and attached to a respective commissure of the three leaflets of the prosthetic valve, with three axial struts 1426B disposed between adjacent commissure posts 1426A. The axial frame members 1426 aid in valve alignment and coaptation. More particularly, the axial frame members 1426 reinforce or strengthen the commissure region of the prosthetic valve 1442 by shaping the leaflets and supporting the leaflets during opening and closing thereof, and thus provide more reliable leaflet coaptation. In addition, the axial frame members 1426 minimize crossing profile of the transcatheter valve prosthesis while maximizing symmetrical cell expansion.

As with the stent 102, the inflow portion 1408 includes exactly three rows of struts 1412 and crowns 1410 between the first ends 1438 of the axial frame members 1426 and the inflow end 1406 of the stent 1402. Further, four struts 1412 and three crowns 1410 are disposed between the first ends 1428 of adjacent axial frame members 1426.

The "no outflow crown" configuration of the stent 1402 maximizes access to the coronary arteries because the axial frame members 1426 are the only structures in the vicinity of the coronary arteries. It is very improbable that the right coronary artery and/or the left main coronary artery will be blocked or jailed by the axial frame members 1426, and thus there will be clear access to the coronary arteries via a coronary guide catheter once the transcatheter valve prosthesis 100 is deployed in situ. Further, the chance of blockage can be further reduced by only including three commissure posts 1426A of the axial frame members 1426, and no axial struts 1426B. In addition, with the elimination of the outflow crowns, the overall height of the stent 1402 may be reduced relative to the overall height of the stent 102. A shorter overall height minimizes interaction with aortic anatomy, thereby resulting in less vessel trauma or valve deformation.

Figure 15:
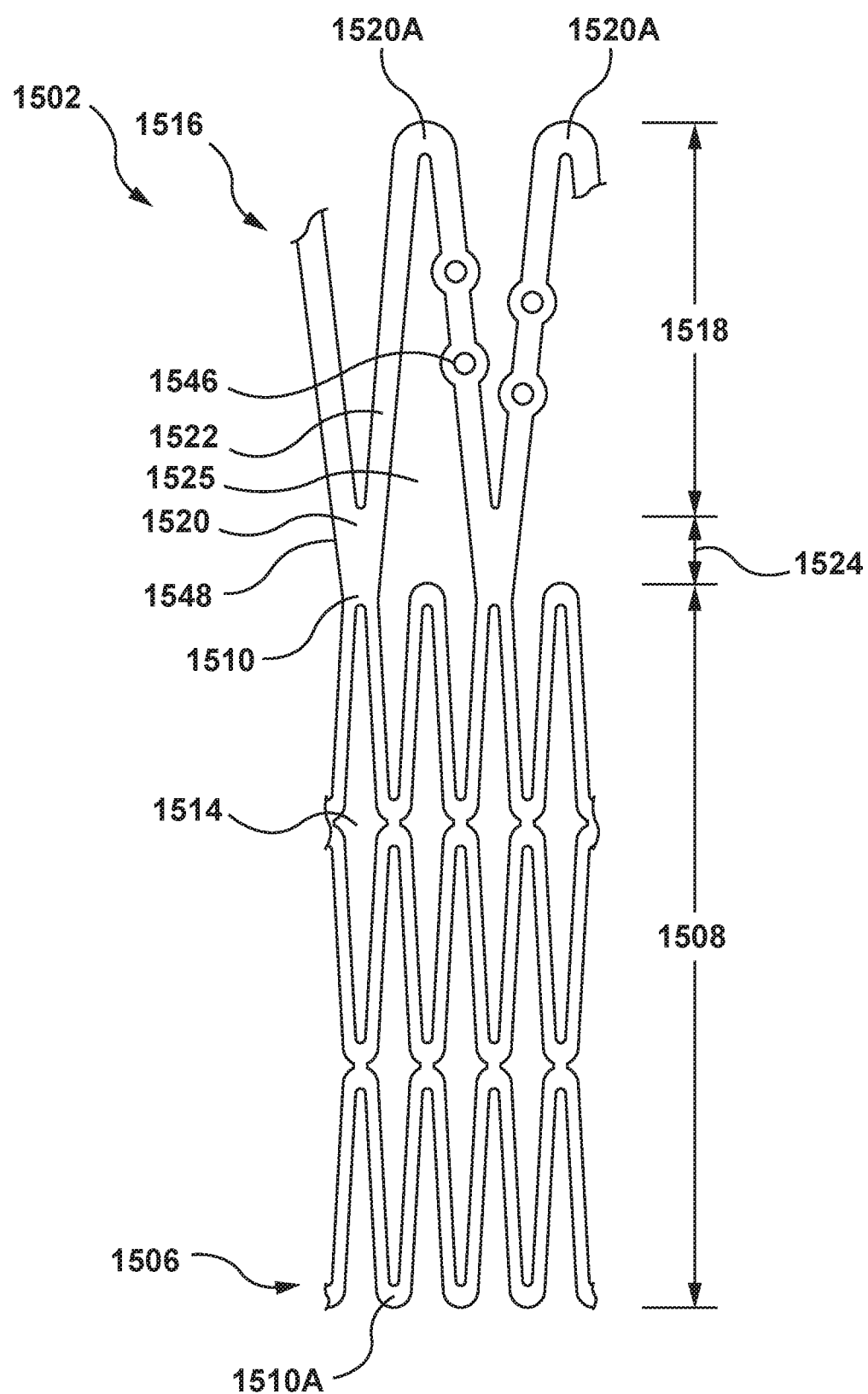
FIG. 15 is a side view of a stent according to another embodiment hereof, wherein the stent is in a non-expanded or crimped configuration and struts of an outflow portion of the stent include holes for attachment to commissures of a prosthetic valve.
Figure 16:
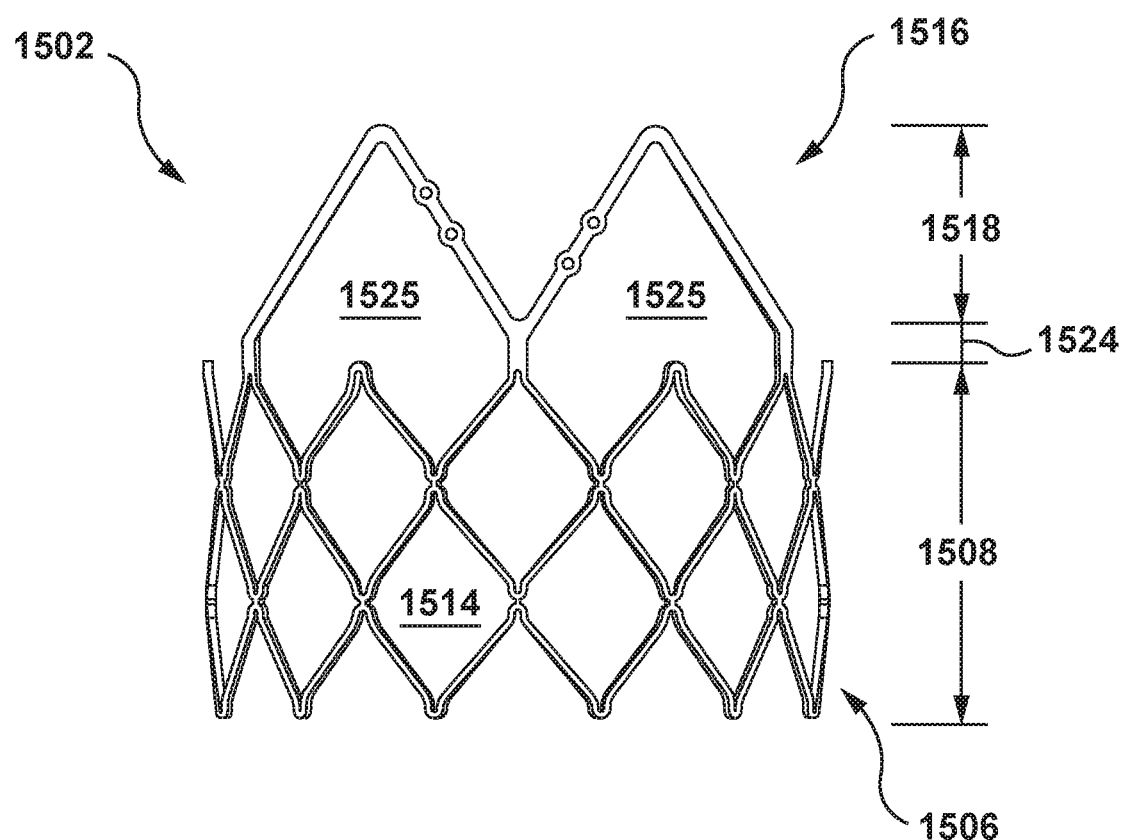
FIG. 16 is a side view of the stent of FIG. 15, wherein the stent is in an expanded configuration.
Figure 17:
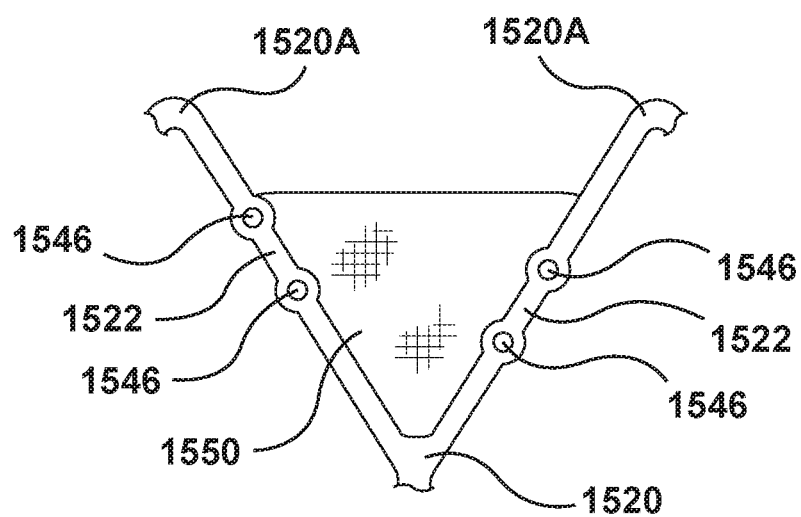
FIG. 17 is an enlarged side view of the stent of FIG. 15, wherein a flap of tissue spans between the struts of the outflow portion of the stent for attachment to commissures of a prosthetic valve.

FIGS. 15, 16, and 17 illustrate a stent 1502 according to another embodiment hereof in which commissure posts are omitted and rather a plurality of material flaps are utilized for attachment to commissures of the prosthetic valve. FIG. 15 is a side view of the stent 1502 in a non-expanded or crimped configuration, while FIG. 16 is a side view of the stent 1502 in an expanded configuration. FIG. 17 is an enlarged side view of the stent 1502 of FIG. 15, and illustrates a material flap 1550 which spans between struts 1522 of the outflow portion 1518 of the stent 1502 for attachment to commissures of a prosthetic valve.

More particularly, the stent 1502 is balloon expandable and includes an inflow portion 1508, an outflow portion 1518, and a transition portion 1524 bridging, connecting, or otherwise extending between the inflow portion 1508 and the outflow portion 1518. The stent 1502 is a tubular component defining a central lumen or passageway (not shown on FIG. 15) and having an inflow or proximal end 1506 and an outflow or distal end 1516. When expanded, a diameter $D_I$ of the inflow end 1506 of the stent 1502 is the same as a diameter $D_O$ of the outflow end 1516 of the stent 1502. The stent 1502 may be formed by a laser-cut manufacturing method and/or another conventional stent forming method as would be understood by one of ordinary skill in the art. The cross-section of the stent 1502 may be circular, ellipsoidal, rectangular, hexagonal, square, or other polygonal shape, although at present it is believed that circular or ellipsoidal may be preferable when utilized with the replacement of an aortic valve.

A prosthetic valve (not shown) is disposed within and secured to at least the outflow portion 1518 of the stent 1502. In addition, the prosthetic valve may also be disposed within and secured to the inflow portion 1508 of the stent 1502. The prosthetic valve is the same as prosthetic valve 132 described above. The inflow portion 1508 is formed proximate to the inflow end 1506 of the stent 1502, and is the same as inflow portion 108 described above. The inflow portion 1508 of the stent 1502 may be formed with nodes 111 having abutting crowns 110 as described in FIGS. 9 and 10 above, or may be formed with shortened nodes 1111 having overlapping crowns 1110 as described in FIGS. 11 and 12 above. Similar to the stent 102, the inflow end 1506 of the stent 1502 has a total of twelve endmost inflow crowns 1510A.

The outflow portion 1518 is formed proximate to the outflow end 1516 of the stent 1502. The outflow portion 1518 is a ring. The outflow portion 1518 includes a plurality of crowns 1520 and a plurality of struts 1522 with each crown 1520 being formed between a pair of opposing struts 1522. Each crown 1520 is a curved segment or bend extending between opposing struts 1522. A series of endmost outflow crowns 1520A are formed at the outflow end 1516 of the stent 1502. Similar to the stent 102, the outflow end 1516 of the stent 1502 has a total of six endmost outflow crowns 1520A. In this embodiment, three pairs of adjacent struts 1522 of the outflow portion 1518 include holes 1546 formed therein. The holes 1546 are utilized in suturing the prosthetic valve into the stent 1502, as will be described in more detail herein with respect to FIG. 17.

The transition portion 1524 bridges, connects, or otherwise extends between the inflow portion 1508 and the outflow portion 1518. The transition portion 1524 includes a total of six reinforced connections 1548, each reinforced connection 1548 extending between an outflow crown 1520 of the outflow portion 1518 and a crown 1510 of the inflow portion 1508. Each reinforced connection 1548 includes extra or added material that surrounds the abutting or opposing crowns 1520, 1510 such that each reinforced connection 1548 has an increased width relative to a width of the plurality of struts 1522 of the outflow portion 1518. In this embodiment, the endmost outflow crowns 1520A are not connected to the reinforced connections 1548 but rather may be considered to be free or unattached while the remaining outflow crowns 1520 of the outflow portion 1518 are connected to the reinforced connections 1548 and disposed closer to the inflow end 1506 than the endmost outflow crowns 1520A.

In the embodiment shown, there is a single row of struts 1522 and crowns 1520 coupled to the reinforced connections 1548 and defining the outflow end 1516 of the stent 1502. Further, in the embodiment shown, exactly two struts 1522 and a single crown 1520 of the outflow portion 1518 are disposed between adjacent reinforced connections 1548. Such an arrangement provides a series of six endmost outflow side openings 1525 formed at the outflow portion 1518 of the stent 1502. Each endmost outflow side opening 1525 is heart-shaped, with each endmost outflow side opening 1525 being defined by two adjacent struts 1522 of the outflow portion 1518, four adjacent struts 1512 of the inflow portion 1508, and two adjacent reinforced connections 1548 of the transition portion 1524. The endmost outflow side openings 1525 of the outflow portion 1518 are relatively larger than a plurality of side openings 1514 of the inflow portion 1508 to improve access to the coronary arteries. More particularly, the endmost outflow side openings 1525 of the outflow portion 1518 are configured to be of sufficient size to be easily crossed with a coronary guide catheter into either the right coronary artery or the left main coronary artery once the transcatheter valve prosthesis is deployed in situ.

As described above, three pairs of adjacent struts 1522 include holes 1546 formed therein that are configured to attach a respective commissure of the three leaflets of the prosthetic valve to the stent 1502. As shown on FIG. 17, a material flap 1550 is attached to the holes 1546 such that the material flap 1550 spans or bridges between the adjacent struts 1522 of the outflow portion 1518. Stent 1502 includes a total of three material flaps 1550. In an embodiment, each material flap 1550 is generally triangular in shape. The three material flaps 1550 are aligned with and attached to a respective commissure of the three leaflets of the prosthetic valve. The material flap 1550 may be formed from a material such as those suitable for graft material 144, such as but not limited to a natural or biological material such as pericardium or another membranous tissue such as intestinal submucosa, a low-porosity woven fabric, such as polyester, Dacron fabric, or PTFE, or a knit or woven polyester, such as a polyester or PTFE knit.

Each material flap 1550 forms a webbing or pad to which a respective commissure of the three leaflets of the prosthetic valve is attached. Since the three material flaps 1550 are aligned with and attached to a respective commissure of the three leaflets of the prosthetic valve, the material flaps 1550 aid in valve alignment and coaptation. Further, in an embodiment, each material flap 1550 may function like a trampoline and absorb shock during diastole. By functioning as a shock absorber, the material flaps 1550 prevent tissue damage, reduce paravalvular leakage, and increase the durability of the prosthetic valve.

As with the stent 102, the inflow portion 1508 includes exactly three rows of struts 1512 and crowns 1510 between the reinforced connections 1548 and the inflow end 1506 of the stent 1502. Further, four struts 1512 and three crowns 1510 are disposed between adjacent reinforced connections 1548.

The overall height of the stent 1502 may be reduced relative to the overall height of stent 102 because the mechanism for commissure attachments reside or are integrated into the outflow portion 1518 of the stent 1502. A shorter overall height minimizes interaction with aortic anatomy, thereby resulting in less vessel trauma or valve deformation. A shorter overall height also improves coronary access, via a coronary guide catheter, to the right coronary artery and left main coronary artery. A shorter overall height (in the crimped state) also improves deliverability.

Figure 18:
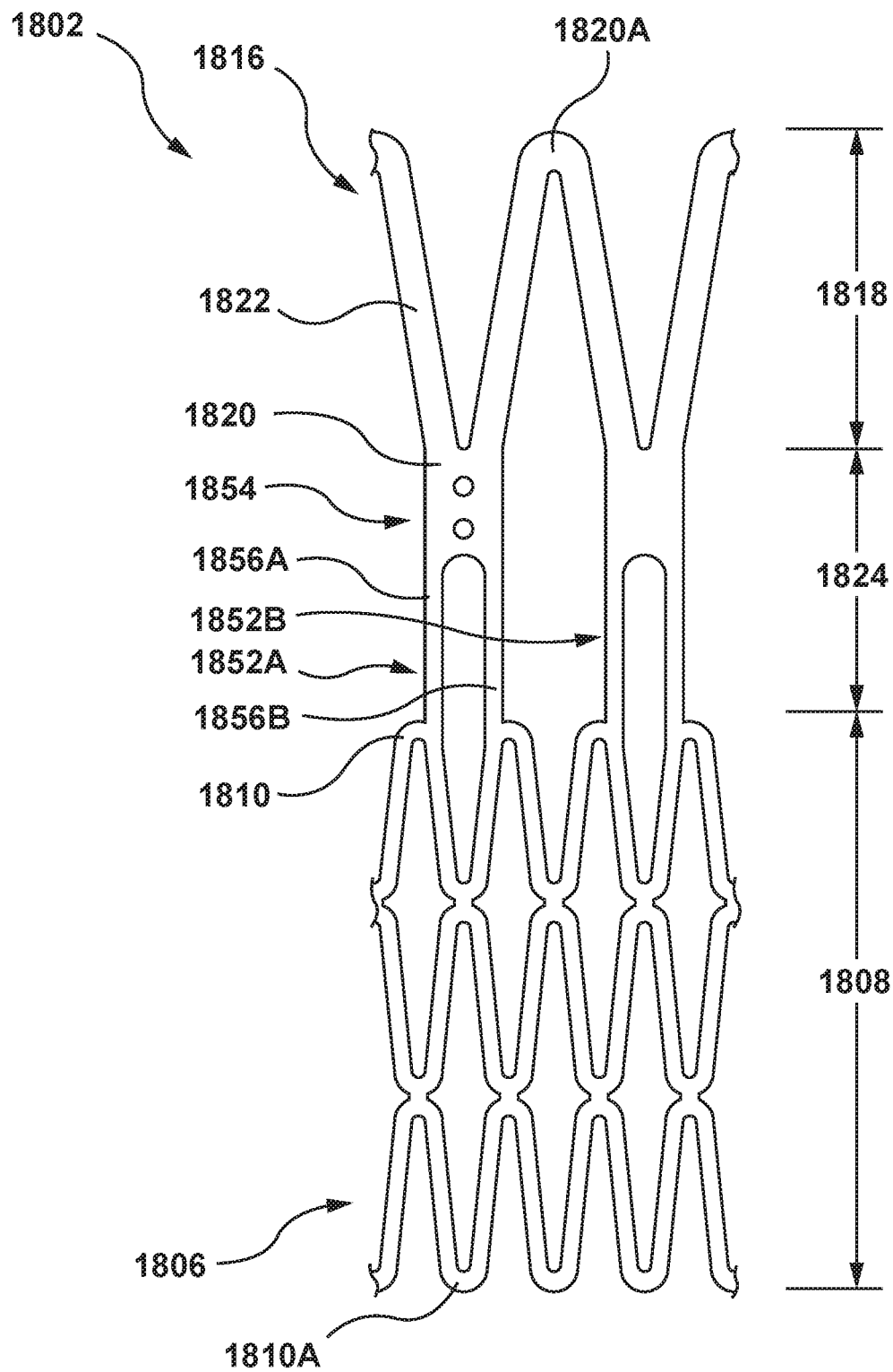
FIG. 18 is a side view of a stent according to another embodiment hereof, wherein the stent is in a non-expanded or crimped configuration and a transition portion of the stent is configured for attachment to commissures of a prosthetic valve.
Figure 19:
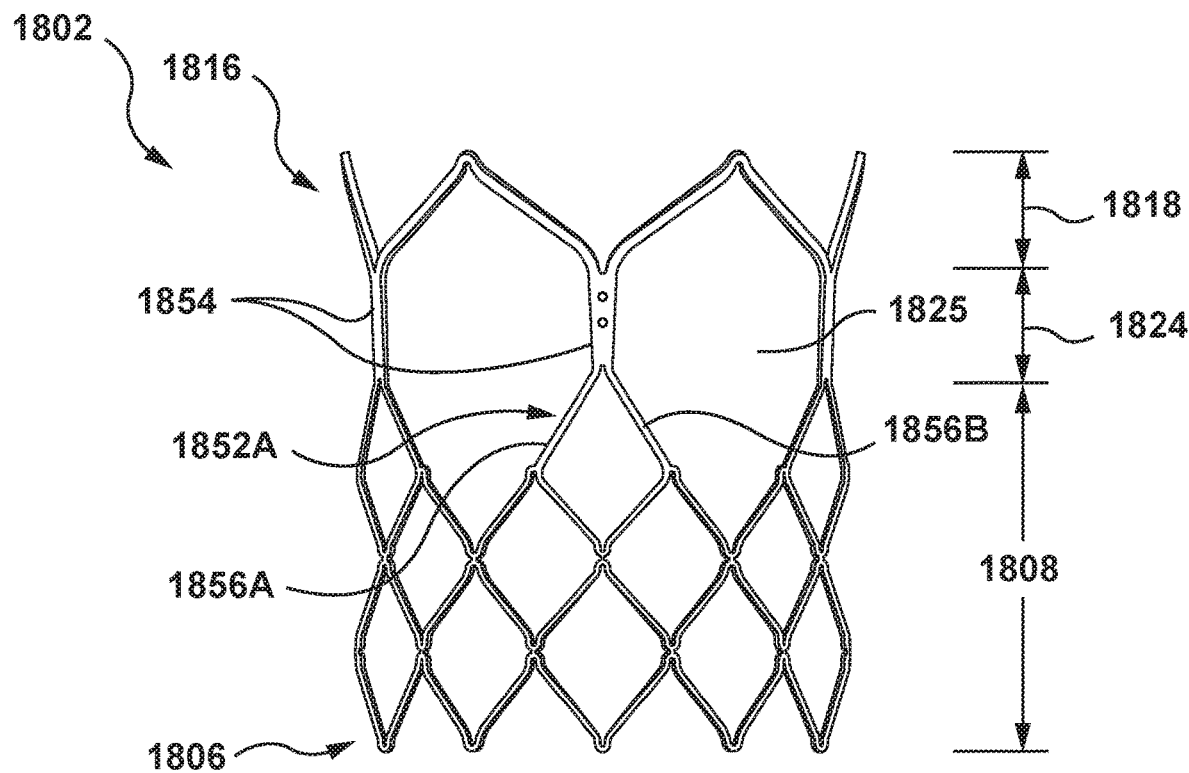
FIG. 19 is a side view of the stent of FIG. 18, wherein the stent is in an expanded configuration.
Figure 20:
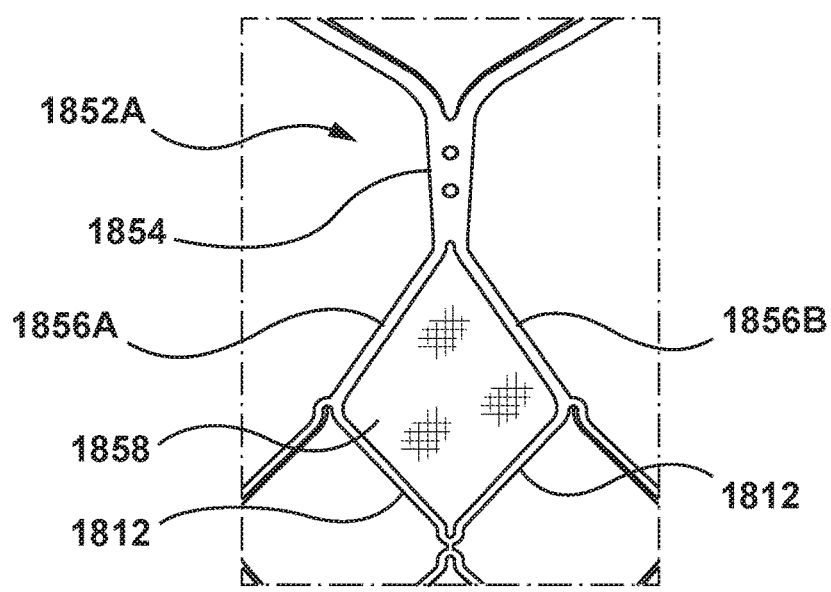
FIG. 20 is an enlarged side view of the stent of FIG. 18, wherein a flap of tissue spans within the transition portion of the stent for attachment to commissures of a prosthetic valve.

FIGS. 18, 19, and 20 illustrate a stent 1802 according to another embodiment hereof in which a plurality of material flaps are utilized for attachment to commissures of the prosthetic valve. The stent 1802 is similar to the stent 1502, except that a transition portion 1824 of the stent 1802 is configured for attachment to commissures of the prosthetic valve rather than the outflow portion 1518 of the stent 1502. FIG. 18 is a side view of the stent 1802 in a non-expanded or crimped configuration, while FIG. 19 is a side view of the stent 1802 in an expanded configuration. FIG. 20 is an enlarged side view of a portion of the stent 1802, and illustrates a material flap 1858 that spans within the transition portion of the stent 1802 for attachment to commissures of a prosthetic valve.

More particularly, the stent 1802 is balloon expandable and includes an inflow portion 1808, an outflow portion 1818, and a transition portion 1824 bridging, connecting, or otherwise extending between the inflow portion 1808 and the outflow portion 1818. The stent 1802 is a tubular component defining a central lumen or passageway (not shown on FIG. 18) and having an inflow or proximal end 1806 and an outflow or distal end 1816. When expanded, a diameter of the inflow end 1806 of the stent 1802 is the same as a diameter of the outflow end 1816 of the stent 1802. The stent 1802 may be formed by a laser-cut manufacturing method and/or another conventional stent forming method as would be understood by one of ordinary skill in the art.

The cross-section of the stent 1802 may be circular, ellipsoidal, rectangular, hexagonal, square, or other polygonal shape, although at present it is believed that circular or ellipsoidal may be preferable when utilized with the replacement of an aortic valve.

A prosthetic valve (not shown) is disposed within and secured to at least the transition portion 1824 of the stent 1802. In addition, the prosthetic valve may also be disposed within and secured to the inflow portion 1808 of the stent 1802. The prosthetic valve is the same as prosthetic valve 132 described above. The inflow portion 1808 is formed proximate to the inflow end 1806 of the stent 1802, and is the same as inflow portion 108 described above. The inflow portion 1808 of the stent 1802 may be formed with nodes 111 having abutting crowns 110 as described in FIGS. 9 and 10 above, or may be formed with shortened nodes 1111 having overlapping crowns 1110 as described in FIGS. 11 and 12 above. Similar to the stent 102, the inflow end 1806 of the stent 1802 has a total of twelve endmost inflow crowns 1810A.

The outflow portion 1818 is formed proximate to the outflow end 1816 of the stent 1802. The outflow portion 1818 is a ring. The outflow portion 1818 includes a plurality of crowns 1820 and a plurality of struts 1822 with each crown 1820 being formed between a pair of opposing struts 1822. Each crown 1820 is a curved segment or bend extending between opposing struts 1822. Similar to the stent 102, a series of endmost outflow crowns 1820A are formed at the outflow end 1816 of the stent 1802. The outflow end 1816 of the stent 1802 has a total of six endmost outflow crowns 1820A.

The transition portion 1824 bridges, connects, or otherwise extends between the inflow portion 1808 and the outflow portion 1818. The transition portion 1824 includes a total of six axial frame members 1852, each axial frame member 1852 extending between an outflow crown 1820 of the outflow portion 1818 and two crowns 1810 of the inflow portion 1808. In the non-expanded or "crimped" configuration, the axial frame members 1852 are substantially parallel to the central longitudinal axis of the stent 1802. Each axial frame member 1852 includes a planar base or block 1854 and two legs 1856A, 1856B longitudinally extending from the planar base 1854. The planar base 1854 has an increased width relative to a width of a strut 1822 of the outflow portion 1818. Legs 1856A, 1856B are spaced apart from each other. Each leg 1856A, 1856B is attached to a crown 1810 of the inflow portion 1808. Stated another way, each leg 1856A, 1856B is a straight segment extending between the planar base 1854 and a crown 1810 of the inflow portion 1808. Legs 1856A, 1856B radially extend from the planar base 1854 when the stent 1802 is in the expanded configuration, as shown on FIG. 19. More particularly, the ends of the legs 1856A, 1856B that are attached to the two crowns 1810 of the inflow portion flare or spread apart when the inflow portion 1808 radially expands. Each axial frame member 1852 is disposed approximately halfway between a pair of adjacent endmost outflow crowns 1820A. Three of the six axial frame members 1852 are commissure posts 1852A and aligned with and attached to a respective commissure of the three leaflets 134 of the prosthetic valve 132. Three of the axial frame members 1854 are axial struts 1854B and are disposed between adjacent commissure posts 1854A.

In this embodiment, the endmost outflow crowns 1820A are not connected to the axial frame members 1852 but rather may be considered to be free or unattached while the remaining outflow crowns 1820 of the outflow portion 1818 are connected to the axial frame members 1852 and disposed closer to the inflow end 1806 than the endmost outflow crowns 1820A. In the embodiment shown, there is a single row of struts 1822 and crowns 1820 coupled to the planar bases 1854 of the axial frame members 1852 and defining the outflow end 1816 of the stent 1802. Further, in the embodiment shown, exactly two struts 1822 and a single crown 1820 of the outflow portion 1818 are disposed between adjacent axial frame members 1852. Such an arrangement provides a series of six endmost outflow side openings 1825 formed at the outflow portion 1818 of the stent 1802. Each endmost outflow side opening 1825 is defined by two adjacent struts 1822 of the outflow portion 1818, two adjacent struts 1812 of the inflow portion 1808, and two adjacent axial frame members 1852 of the transition portion 1824. The endmost outflow side openings 1825 of the outflow portion 1818 are relatively larger than the plurality of side openings 1814 of the inflow portion 1808 to improve access to the coronary arteries. More particularly, the endmost outflow side openings 1825 of the outflow portion 1818 are configured to be of sufficient size to be easily crossed with a coronary guide catheter into either the right coronary artery or the left main coronary artery once the transcatheter valve prosthesis is deployed in situ.

As described above, the transition portion 1824 of the stent 1802 is configured for attachment to commissures of the prosthetic valve. As shown on FIG. 20, a material flap 1858 is attached to three commissure posts 1852A. Stated another way, stent 1802 includes a total of three material flaps 1858. The three material flaps 1858 are aligned with and attached to a respective commissure of the three leaflets of the prosthetic valve. In an embodiment, each material flap 1858 is generally diamond-shaped. Each material flap 1858 spans or bridges between legs 1856A, 1856B and two adjacent struts 1812 of the inflow portion 1808. In this embodiment, the entire perimeter of each material flap 1858 is connected to the stent 1802. The material flap 1858 may be formed from a material such as those suitable for graft material 144, such as but not limited to a natural or biological material such as pericardium or another membranous tissue such as intestinal submucosa, a low-porosity woven fabric, such as polyester, Dacron fabric, or PTFE, or a knit or woven polyester, such as a polyester or PTFE knit.

Each material flap 1858 forms a webbing or pad to which a respective commissure of the three leaflets of the prosthetic valve is attached. Since the three material flaps 1858 are aligned with and attached to a respective commissure of the three leaflets of the prosthetic valve, the material flaps 1858 aid in valve alignment and coaptation. Further, in an embodiment, each material flap 1858 may function like a trampoline and absorb shock during diastole. By functioning as a shock absorber, the material flaps 1858 prevent tissue damage, reduce paravalvular leakage, and increase the durability of the prosthetic valve.

As with the stent 102, the inflow portion 1808 includes exactly three rows of struts 1812 and crowns 1810 between the axial frame members 1852 and the inflow end 1806 of the stent 1802. Further, in this embodiment, two struts 1812 and one crown 1810 are disposed between adjacent axial frame members 1852. In an embodiment, a height or length of the stent 1802 in the expanded configuration is 24 mm, the height being measured from the most proximal part thereof to the most distal part thereof.

Figure 21:
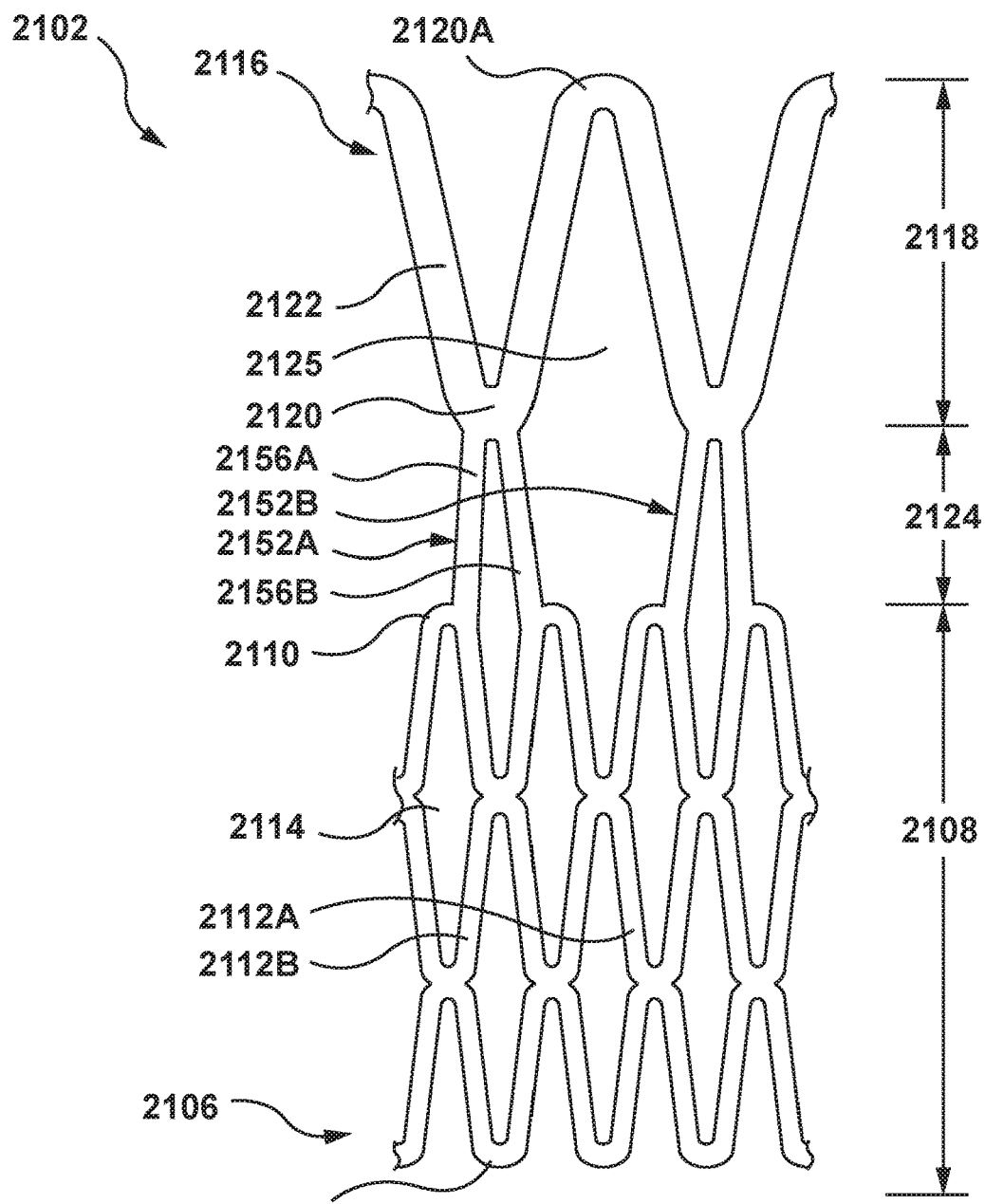
FIG. 21 is a side view of a stent according to another embodiment hereof, wherein the stent is in a non-expanded or crimped configuration and a transition portion of the stent is configured for attachment to commissures of a prosthetic valve.
Figure 22:
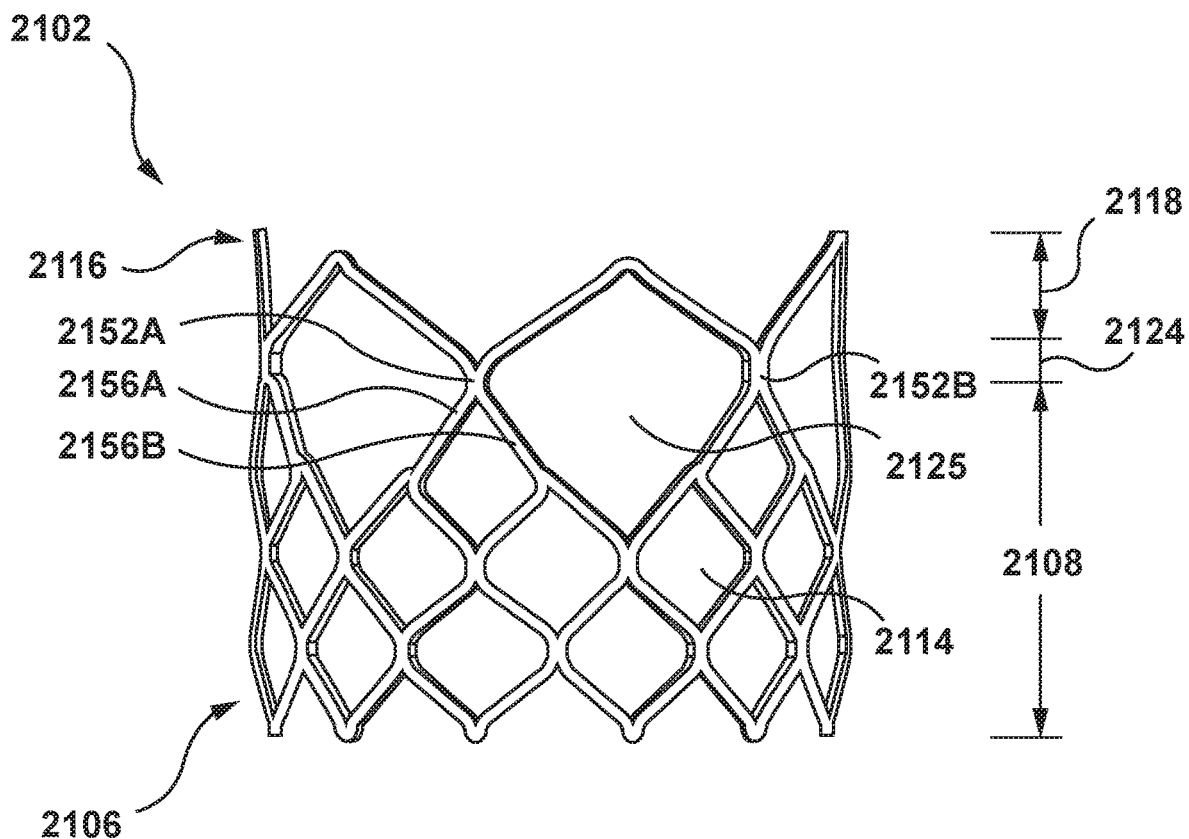
FIG. 22 is a side view of the stent of FIG. 21, wherein the stent is in an expanded configuration.
Figure 23:
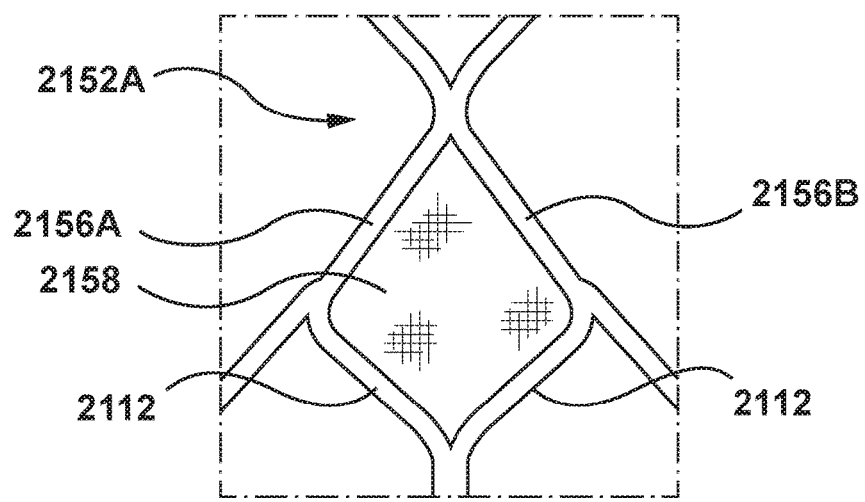
FIG. 23 is an enlarged side view of the stent of FIG. 21, wherein a flap of tissue spans within the transition portion of the stent for attachment to commissures of a prosthetic valve.

FIGS. 21, 22, and 23 illustrate a stent 2102 according to another embodiment hereof in which a plurality of material flaps are utilized for attachment to commissures of the prosthetic valve. The stent 2102 is similar to the stent 1802, except that a transition portion 2124 of the stent 2102 has a different configuration than the transition portion 1824 of the stent 1802. FIG. 21 is a side view of the stent 2102 in a non-expanded or crimped configuration, while FIG. 22 is a side view of the stent 2102 in an expanded configuration. FIG. 23 is an enlarged side view of the stent 2102 of FIG. 21, and illustrates a material flap 2158 that spans within the transition portion of the stent 2102 for attachment to commissures of a prosthetic valve.

More particularly, the stent 2102 is balloon expandable and includes an inflow portion 2108, an outflow portion 2118, and a transition portion 2124 bridging, connecting, or otherwise extending between the inflow portion 2108 and the outflow portion 2118. The stent 2102 is a tubular component defining a central lumen or passageway (not shown on FIG. 21) and having an inflow or proximal end 2106 and an outflow or distal end 2116. When expanded, a diameter of the inflow end 2106 of the stent 2102 is the same as a diameter of the outflow end 2116 of the stent 2102. The stent 2102 may be formed by a laser-cut manufacturing method and/or another conventional stent forming method as would be understood by one of ordinary skill in the art. The cross-section of the stent 2102 may be circular, ellipsoidal, rectangular, hexagonal, square, or other polygonal shape, although at present it is believed that circular or ellipsoidal may be preferable when utilized with the replacement of an aortic valve.

A prosthetic valve (not shown) is disposed within and secured to at least the transition portion 2124 of the stent 2102. In addition, the prosthetic valve may also be disposed within and secured to the inflow portion 2108 of the stent 2102. The prosthetic valve is the same as prosthetic valve 132 described above. The inflow portion 2108 is formed proximate to the inflow end 2106 of the stent 2102. The inflow portion 2108 of the stent 2102 may be formed with nodes 111 having abutting crowns 110 as described in FIGS. 9 and 10 above, or may be formed with shortened nodes 1111 having overlapping crowns 1110 as described in FIGS. 11 and 12 above. Similar to the stent 102, the inflow end 2106 of the stent 2102 has a total of twelve endmost inflow crowns 2110A.

Figure 21A:
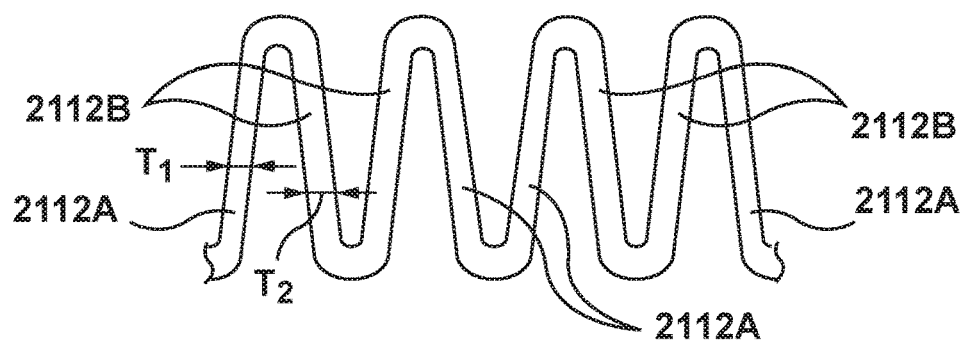
FIG. 21A is an enlarged side view of a portion of an inflow portion of the stent of FIG. 21, wherein the stent is in the non-expanded or crimped configuration.

The inflow portion 2108 is the same as the inflow portion 108 described above, except that the inflow portion 2108 includes struts 2112 that have varying thicknesses. More particularly, as best shown in FIG. 21A which is an enlarged view of a portion of the inflow portion 2108 of the stent 2102, pairs of struts 2112 of the inflow portion 2108 alternate between a first thickness T1 and a second thickness T2, the second thickness T2 being greater than the first thickness T1. For illustrative purposes only, the struts 2112 of the inflow portion 2108 are labeled as struts 2112A having the first thickness T1 and struts 2112B having the second thickness T2. In an embodiment, the first thickness T1 may be 0.32 mm and the second thickness may be 0.38 mm. The varying thicknesses of the struts 2112 enhance cell symmetry when the stent 2102 is expanded. Stated another way, the varying thicknesses of the struts 2112 configure the stent 2102 to exhibit more uniform cell expansion than when the struts 2112 are formed with unitary thicknesses. Symmetrical cell expansion ensures that the stent 2102 crimps well onto a balloon of a balloon catheter for delivery. Poor crimp quality may lead to portions of the stent overlapping when crimped, which in turn may cause tissue damage to the valve leaflets of the prosthetic valve during the crimping process. In another embodiment, however, the struts 2112 may alternatively be formed within uniform strut thickness. Further, any embodiment described herein may include an inflow portion having varying strut thickness as shown in the embodiment of FIG. 21 and FIG. 21A.

The outflow portion 2118 is formed proximate to the outflow end 2116 of the stent. The outflow portion 2118 is a ring. The outflow portion 2118 includes a plurality of crowns 2120 and a plurality of struts 2122 with each crown 2120 being formed between a pair of opposing struts 2122. Each crown 2120 is a curved segment or bend extending between opposing struts 2122. A series of endmost outflow crowns 2120A are formed at the outflow end 2116 of the stent 2102. Similar to the stent 102, the outflow end 2116 of the stent 2102 has a total of six endmost outflow crowns 2120A.

The transition portion 2124 bridges, connects, or otherwise extends between the inflow portion 2108 and the outflow portion 2118. The transition portion 2124 includes a total of six axial frame members 2152, each axial frame member 2152 extending between a crown 2120 of the outflow portion 2118 and two crowns 2110 of the inflow portion 2108. Each axial frame member 2152 includes two spaced apart legs 2156A, 2156B that radially and longitudinally extend from an outflow crown 2120 of the outflow portion 2118. Each leg 2156A, 2156B is further attached to a crown 2110 of the inflow portion 2108. Stated another way, each leg 2156A, 2156B is a straight segment extending between an outflow crown 2120 of the outflow portion 2118 and a crown 2110 of the inflow portion 2108. Each axial frame member 2152 is disposed approximately halfway between a pair of adjacent endmost outflow crowns 2120A. Three of the six axial frame members 2152 are commissure posts 2152A and aligned with and attached to a respective commissure of the three leaflets 134 of the prosthetic valve 132. Three of the axial frame members 2152 are axial struts 2152B and are disposed between adjacent commissure posts 2152A.

In this embodiment, the endmost outflow crowns 2120A are not connected to the axial frame members 2152 but rather may be considered to be free or unattached while the remaining outflow crowns 2120 of the outflow portion 2118 are connected to the axial frame members 2152 and disposed closer to the inflow end 2106 than the endmost outflow crowns 2120A. In the embodiment shown, there is a single row of struts 2122 and crowns 2120 coupled to the axial frame members 2154 and defining the outflow end 2116 of the stent 2102. Further, in the embodiment shown, exactly two struts 2122 and a single crown 2120 of the outflow portion 2118 are disposed between adjacent axial frame members 2152. Such an arrangement provides a series of six endmost outflow side openings 2125 formed at the outflow portion 2118 of the stent 2102. Each endmost outflow side opening 2125 is defined by two adjacent struts 2122 of the outflow portion 2118, two adjacent struts 2112 of the inflow portion 2108, and two adjacent axial frame members 2152 of the transition portion 2124. The endmost outflow side openings 2125 of the outflow portion 2118 are relatively larger than a plurality of side openings 2114 of the inflow portion 2108 to improve access to the coronary arteries. More particularly, the endmost outflow side openings 2125 of the outflow portion 2118 are configured to be of sufficient size to be easily crossed with a coronary guide catheter into either the right coronary artery or the left main coronary artery once the transcatheter valve prosthesis is deployed in situ.

As described above, the transition portion 2124 of the stent 2102 is configured for attachment to commissures of the prosthetic valve. As shown on FIG. 23, a material flap 2158 is attached to three commissure posts 2152A. Stated another way, stent 2102 includes a total of three material flaps 2158. The three material flaps 2158 are aligned with and attached to a respective commissure of the three leaflets of the prosthetic valve. In an embodiment, each material flap 2158 is generally diamond-shaped. Each material flap 2158 spans or bridges between legs 2156A, 2156B and two adjacent struts 2112 of the inflow portion 2108. In this embodiment, the entire perimeter of each material flap 2158 is connected to the stent 2102. The material flap 2158 may be formed from a material such as those suitable for graft material 144, such as but not limited to a natural or biological material such as pericardium or another membranous tissue such as intestinal submucosa, a low-porosity woven fabric, such as polyester, Dacron fabric, or PTFE, or a knit or woven polyester, such as a polyester or PTFE knit.

Each material flap 2158 forms a webbing or pad to which a respective commissure of the three leaflets of the prosthetic valve is attached. Since the three material flaps 2158 are aligned with and attached to a respective commissure of the three leaflets of the prosthetic valve, the material flaps 2158 aid in valve alignment and coaptation. Further, in an embodiment, each material flap 2158 may function like a trampoline and absorb shock during diastole. By functioning as a shock absorber, the material flaps 2158 prevent tissue damage, reduce paravalvular leakage, and increase the durability of the prosthetic valve.

As with the stent 102, the inflow portion 2108 includes exactly three rows of struts 2112 and crowns 2110 between the axial frame members 2152 and the inflow end 2106 of the stent 2102. Further, in this embodiment, two struts 2112 and one crown 2110 are disposed between the adjacent axial frame members 2152. In an embodiment, a height or length of the stent 2102 in the expanded configuration is between 22-24 mm, the height being measured from the most proximal part thereof to the most distal part thereof.

Figure 24:
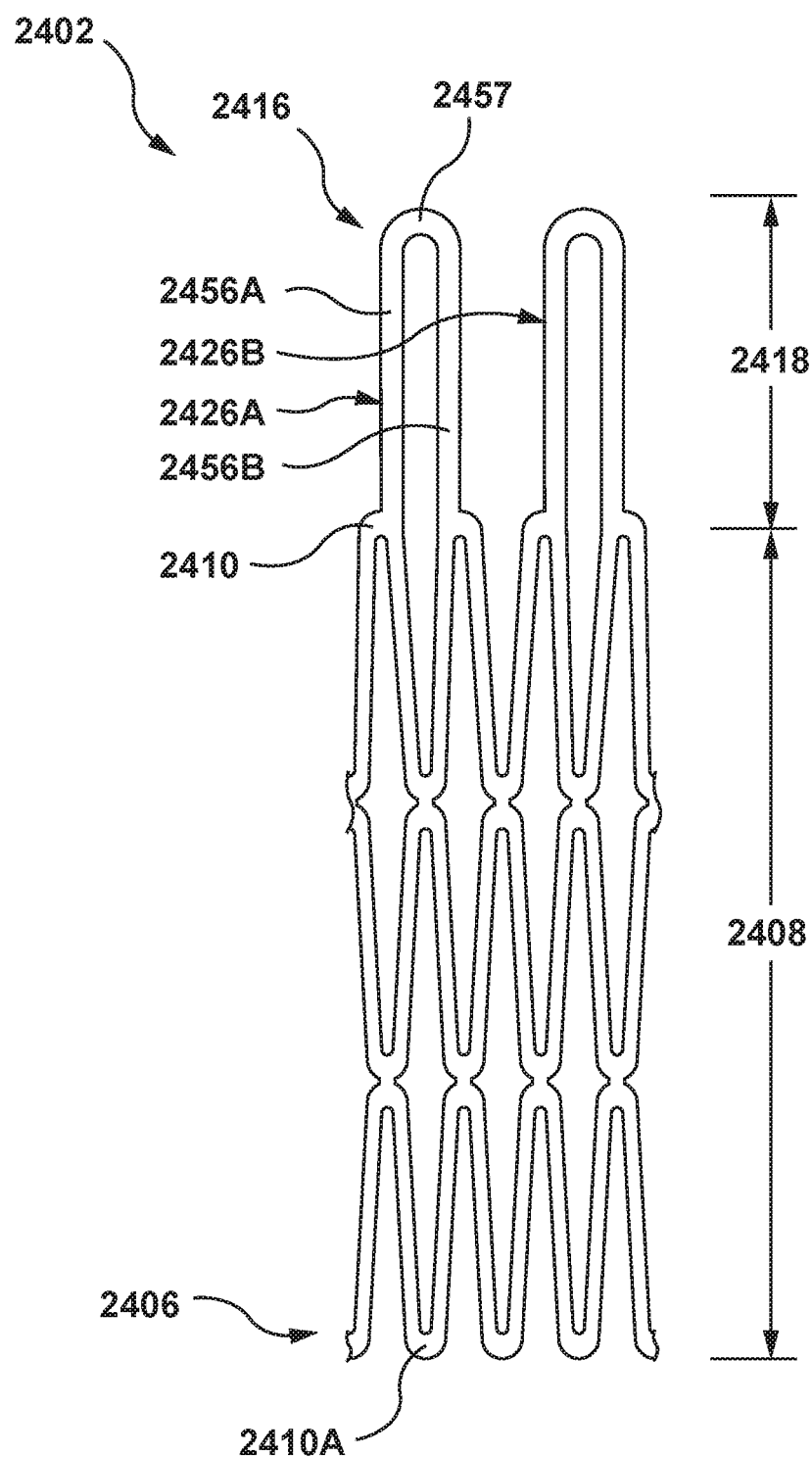
FIG. 24 is a side view of a stent according to another embodiment hereof, wherein the stent is in a non-expanded or crimped configuration and an outflow portion of the stent is configured for attachment to commissures of a prosthetic valve.
Figure 25:
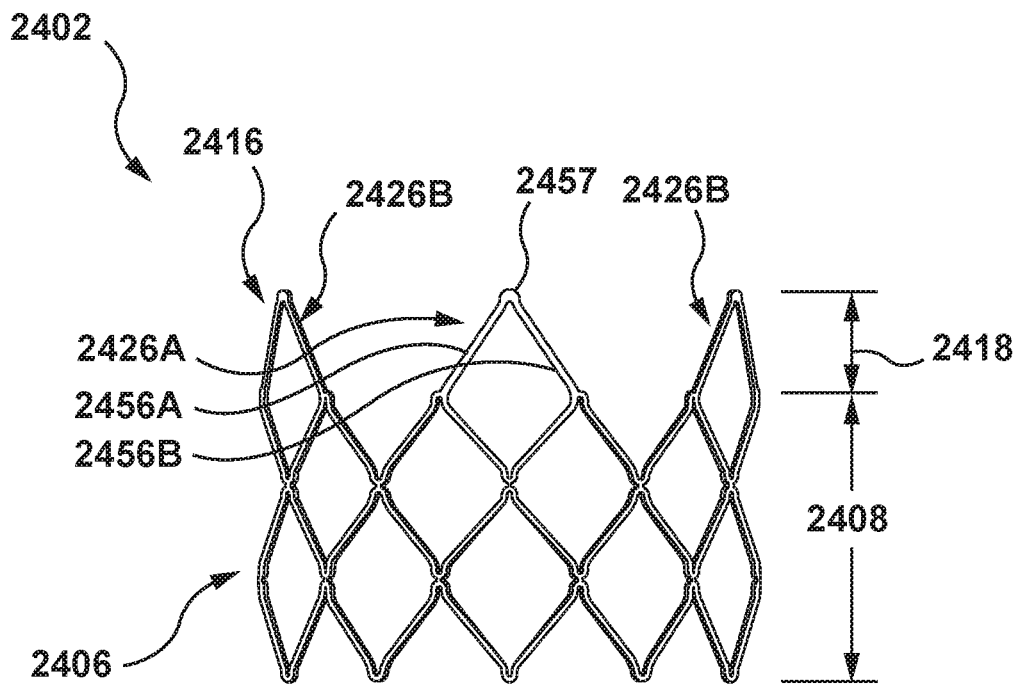
FIG. 25 is a side view of the stent of FIG. 24, wherein the stent is in an expanded configuration.
Figure 26:
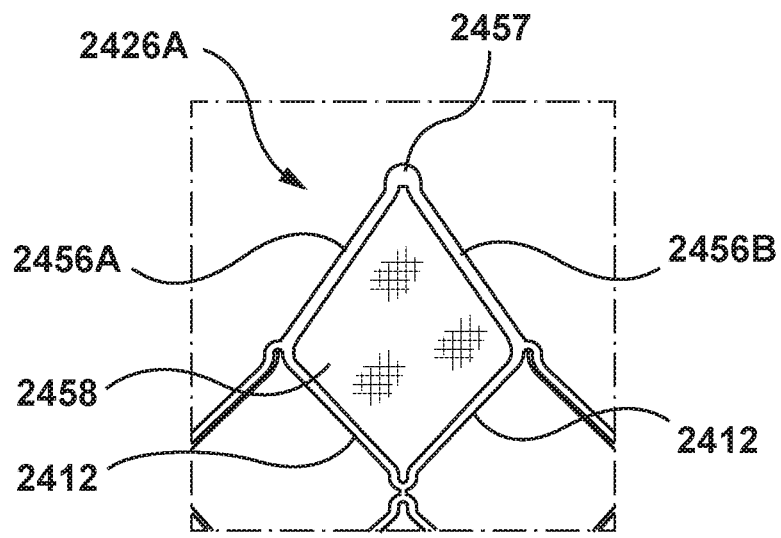
FIG. 26 is an enlarged side view of the stent of FIG. 24, wherein a flap of tissue spans within the outflow portion of the stent for attachment to commissures of a prosthetic valve.

FIGS. 24, 25, and 26 illustrate a stent 2402 according to another embodiment hereof in which a plurality of material flaps are utilized for attachment to commissures of the prosthetic valve. Further, an outflow portion 2418 of a stent 2402 does not include crowns. FIG. 24 is a side view of the stent 2402 in a non-expanded or crimped configuration, while FIG. 22 is a side view of the stent 2402 in an expanded configuration. FIG. 23 is an enlarged side view of the stent 2402 of FIG. 24, and illustrates a material flap spans within the outflow portion 2418 of the stent 2402 for attachment to commissures of a prosthetic valve.

More particularly, the stent 2402 is balloon expandable and includes an inflow portion 2408 and the outflow portion 2418. The stent 2402 is a tubular component defining a central lumen or passageway (not shown on FIG. 24) and having an inflow or proximal end 2406 and an outflow or distal end 2416. When expanded, a diameter of the inflow end 2406 of the stent 2402 is the same as a diameter of the outflow end 2416 of the stent 2402. The stent 2402 may be formed by a laser-cut manufacturing method and/or another conventional stent forming method as would be understood by one of ordinary skill in the art. The cross-section of the stent 2402 may be circular, ellipsoidal, rectangular, hexagonal, square, or other polygonal shape, although at present it is believed that circular or ellipsoidal may be preferable when utilized with the replacement of an aortic valve.

A prosthetic valve (not shown) is disposed within and secured to at least the outflow portion 2418 of the stent 2402. In addition, the prosthetic valve may also be disposed within and secured to the inflow portion 2408 of the stent 2402. The prosthetic valve is the same as prosthetic valve 132 described above. The inflow portion 2408 is formed proximate to the inflow end 2406 of the stent 2402, and is the same as inflow portion 108 described above. The inflow portion 2408 of the stent 2402 may be formed with nodes 111 having abutting crowns 110 as described in FIGS. 9 and 10 above, or may be formed with shortened nodes 1111 having overlapping crowns 1110 as described in FIGS. 11 and 12 above. Similar to the stent 102, the inflow end 2406 of the stent 2402 has a total of twelve endmost inflow crowns 2410A.

The outflow portion 2418 is formed proximate to the outflow end 2416 of the stent 2402. The outflow portion 2418 includes a minimum of three axial frame members 2426. In an embodiment, the outflow portion 2418 includes up to six axial frame members 2426, with three of the axial frame members 2426 being commissure posts 2426A. Each axial frame member 2426 is a U-shaped segment that longitudinally extends from two crowns 2410 of the inflow portion 2408. More particularly, each commissure bar 2426 is a U-shaped segment having two opposing arm segments 2456A, 2456B and a curved segment or bend 2457 extending therebetween. Three of the axial frame members 2426 are commissure posts 2426A circumferentially spaced apart and aligned with and attached to a respective commissure of the three leaflets of the prosthetic valve, with three axial struts 2426B disposed between adjacent commissure posts 2426A. The axial frame members 2426 aid in valve alignment and coaptation. More particularly, the axial frame members 2426 reinforce or strengthen the commissure region of the prosthetic valve 2442 by shaping the leaflets and supporting the leaflets during opening and closing thereof, and thus provide more reliable leaflet coaptation.

As shown on FIG. 26, a material flap 2458 is attached to three commissure posts 2426A. Stated another way, the stent 2402 includes a total of three material flaps 2458. The three material flaps 2458 are aligned with and attached to a respective commissure of the three leaflets of the prosthetic valve. In an embodiment, each material flap 2458 is generally diamond-shaped. Each material flap 2458 spans or bridges between arm segments 2456A, 2456B and two adjacent struts 2412 of the inflow portion 2408. In this embodiment, the entire perimeter of each material flap 2458 is connected to the stent 2402. The material flap 2458 may be formed from a material such as those suitable for graft material 244, such as but not limited to a natural or biological material such as pericardium or another membranous tissue such as intestinal submucosa, a low-porosity woven fabric, such as polyester, Dacron fabric, or PTFE, or a knit or woven polyester, such as a polyester or PTFE knit.

Each material flap 2458 forms a webbing or pad to which a respective commissure of the three leaflets of the prosthetic valve is attached. Since the three material flaps 2458 are aligned with and attached to a respective commissure of the three leaflets of the prosthetic valve, the material flaps 2458 aid in valve alignment and coaptation. Further, in an embodiment, each material flap 2458 may function like a trampoline and absorb shock during diastole. By functioning as a shock absorber, the material flaps 2458 prevent tissue damage, reduce paravalvular leakage, and increase the durability of the prosthetic valve.

As with the stent 102, the inflow portion 2408 includes exactly three rows of struts 2412 and crowns 2410 between the axial frame members 2426 and the inflow end 2406 of the stent 2402. Further, two struts 2412 and one crown 2410 are disposed between adjacent axial frame members 2426.

In addition, the "no outflow crown" configuration of the stent 2402 maximizes access to the coronary arteries because the axial frame members 2426 are the only structures in the vicinity of the coronary arteries. It is very improbable that the right coronary artery and/or the left main coronary artery will be blocked or jailed by the three axial frame members 2426, and thus there will be clear access to the coronary arteries via a coronary guide catheter once the transcatheter valve prosthesis 100 is deployed in situ. Further, the chance of blockage can be further reduced by only including three commissure posts 2426A of the axial frame members 2426, and no axial struts 2426B. In addition, with the elimination of the outflow crowns, the overall height of the stent 2402 may be reduced relative to the overall height of stent 102. A shorter overall height minimizes interaction with aortic anatomy, thereby resulting in less vessel trauma or valve deformation.

Figure 27:
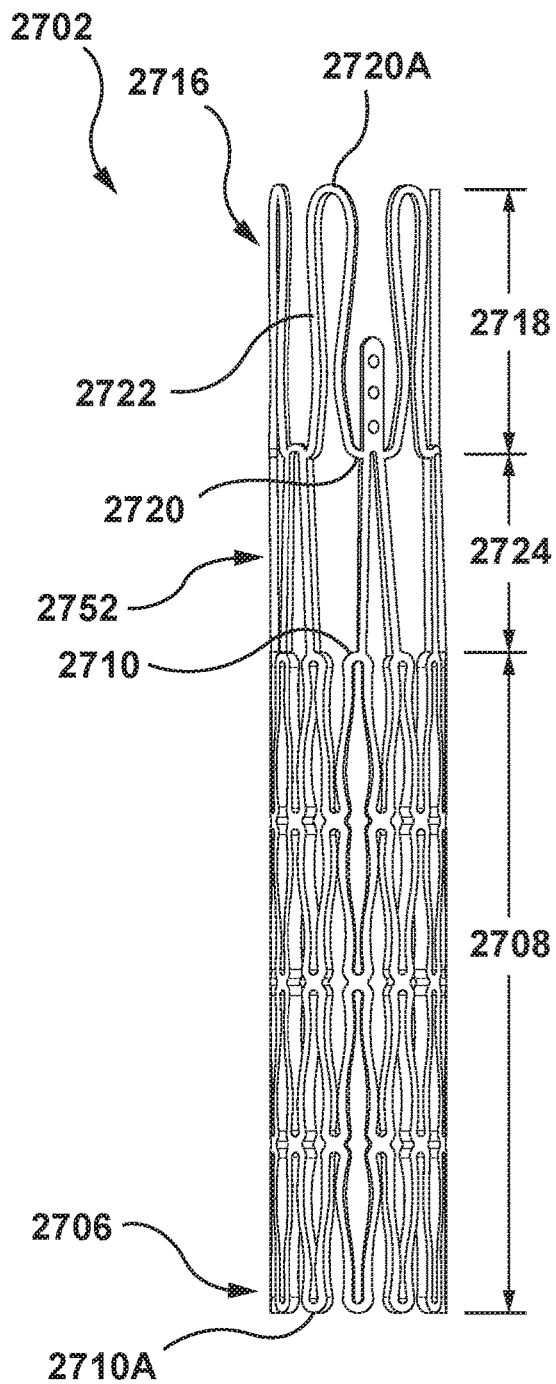
FIG. 27 is a side view of a stent according to another embodiment hereof, wherein the stent is in a crimped configuration and the stent includes an s-shaped strut.
Figure 27A:
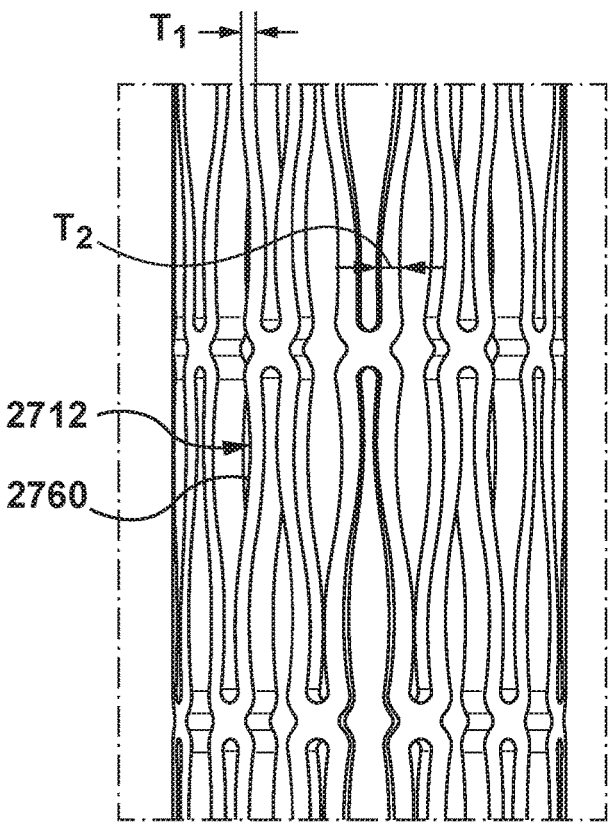
FIG. 27A is an enlarged side view of a portion of the stent of FIG. 27, wherein the stent is in a non-expanded or crimped configuration.
Figure 28:
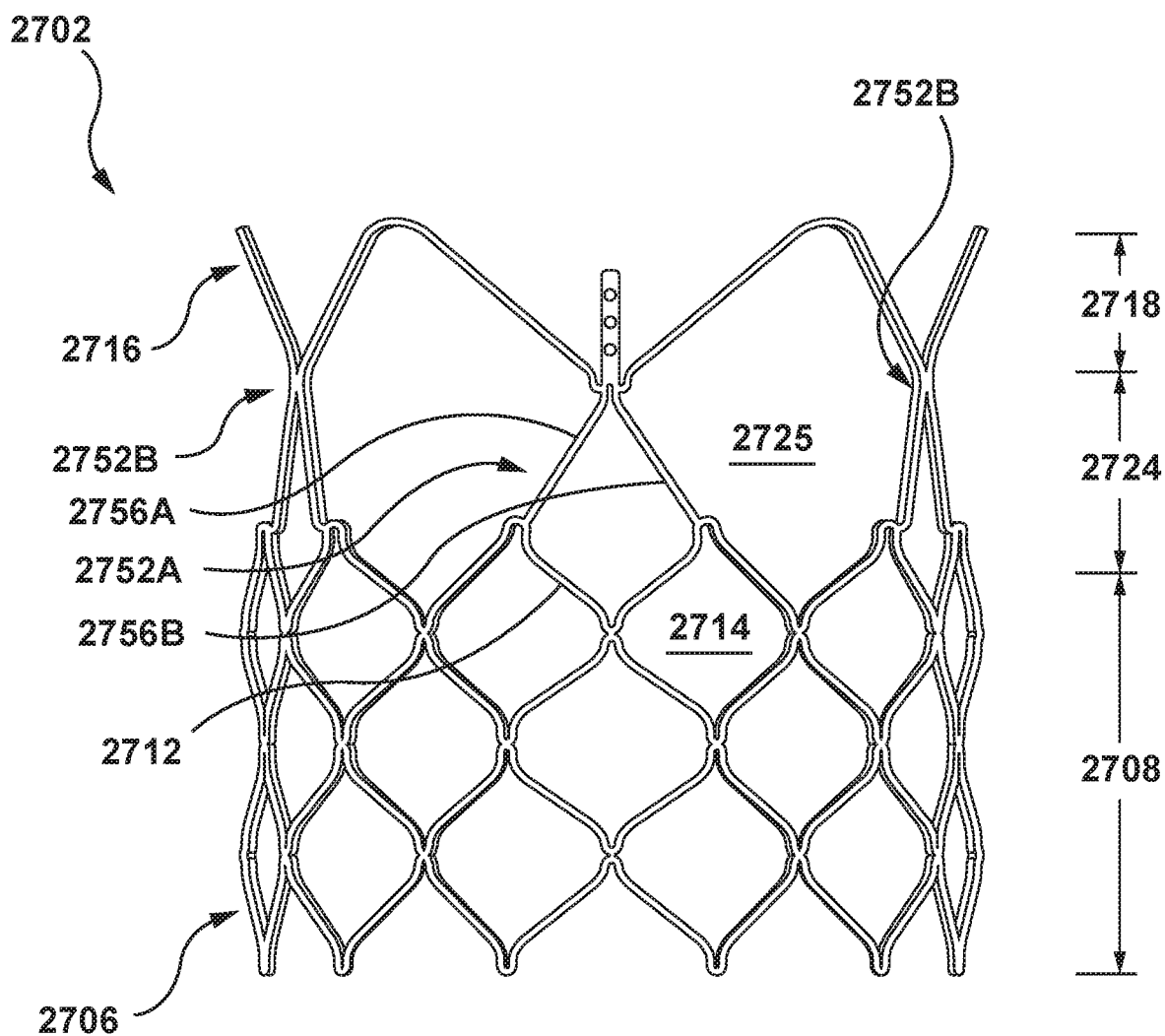
FIG. 28 is a side view of the stent of FIG. 27, wherein the stent is in an expanded configuration.
Figure 29:
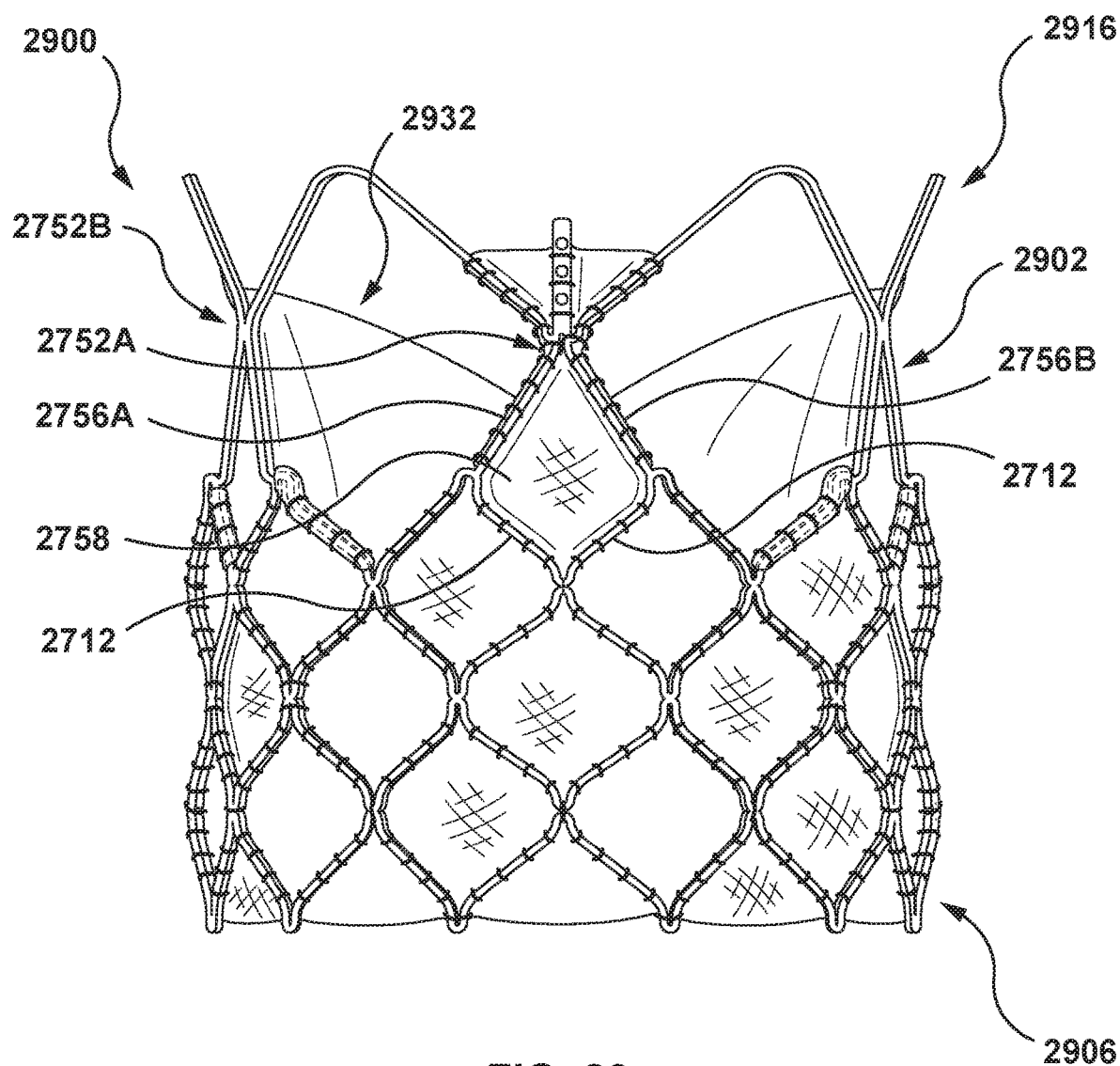
FIG. 29 is a side view of a transcatheter valve prosthesis including the stent of FIG. 27, wherein a flap of tissue spans within the transition portion of the stent for attachment to commissures of a prosthetic valve.

FIGS. 27, 27A, 28, and 29 illustrate a stent 2702 according to another embodiment hereof in which a plurality of material flaps are utilized for attachment to commissures of the prosthetic valve. The stent 2702 is similar to the stent 2102, except that the stent 2702 further includes tapered struts integrally formed therein. FIG. 27 is a side view of the stent 2702 in a crimped configuration, while FIG. 28 is a side view of the stent 2702 in an expanded configuration. FIG. 27A is an enlarged side view of a portion of the stent 2702 of FIG. 27 in a non-expanded or "crimped" configuration. FIG. 29 is a side view of a transcatheter valve prosthesis 2700 in an expanded configuration, the transcatheter valve prosthesis 2700 including the stent 2702, and illustrates a material flap 2758 that spans within the transition portion of the stent 2702 for attachment to commissures of a prosthetic valve.

More particularly, the stent 2702 is balloon expandable and includes an inflow portion 2708, an outflow portion 2718, and a transition portion 2724 bridging, connecting, or otherwise extending between the inflow portion 2708 and the outflow portion 2718. The stent 2702 is a tubular component defining a central lumen or passageway (not shown on FIG. 27) and having an inflow or proximal end 2706 and an outflow or distal end 2716. When expanded, a diameter of the inflow end 2706 of the stent 2702 is the same as a diameter of the outflow end 2716 of the stent 2702. The stent 2702 may be formed by a laser-cut manufacturing method and/or another conventional stent forming method as would be understood by one of ordinary skill in the art. The cross-section of the stent 2702 may be circular, ellipsoidal, rectangular, hexagonal, square, or other polygonal shape, although at present it is believed that circular or ellipsoidal may be preferable when utilized with the replacement of an aortic valve.

A prosthetic valve (not shown) is disposed within and secured to at least the transition portion 2724 of the stent 2702. In addition, the prosthetic valve may also be disposed within and secured to the inflow portion 2708 of the stent 2702. The prosthetic valve is the same as prosthetic valve 132 described above. The inflow portion 2708 is formed proximate to the inflow end 2706 of the stent 2702. The inflow portion 2708 of the stent 2702 may be formed with nodes 111 having abutting crowns 110 as described in FIGS. 9 and 10 above, or may be formed with shortened nodes 1111 having overlapping crowns 1110 as described in FIGS. 11 and 12 above. Similar to the stent 102, the inflow end 2706 of the stent 2702 has a total of twelve endmost inflow crowns 2710A.

In this embodiment, the inflow portion 2708 includes tapered struts 2712 integrally formed therein. Tapered struts 2712 has a varying thickness along a length thereof such that a middle portion is relatively thinner than opposing end portions of the tapered strut 2712. More particularly, tapered struts 2712 have a thinner cross section in the middle of the length thereof as compared to the cross section at the opposing end portions thereof. As best shown on FIG. 27A, which is an enlarged side view of a portion of the inflow portion 2708 of the stent 2702, a middle or center portion 2760 of the tapered strut 2712 has a first thickness T1 while the end portions of the tapered strut 2712 has a second thickness T2, the second thickness T2 being greater than the first thickness T1. In an embodiment, the first thickness T1 may be 0.32 mm and the second thickness may be 0.38 mm. The tapered struts 2712 result in wider side openings 2714 and allow for graft material to better pack within the wider side openings 2714 when the transcatheter valve prosthesis 2700 is crimped onto a balloon for delivery, thereby resulting in a reduced crossing profile.

The outflow portion 2718 is formed proximate to the outflow end 2716 of the stent 2702. The outflow portion 2718 is a ring. The outflow portion 2718 includes a plurality of crowns 2720 and a plurality of struts 2722 with each crown 2720 being formed between a pair of opposing struts 2722. Each crown 2720 is a curved segment or bend extending between opposing struts 2722. A series of endmost outflow crowns 2720A are formed at the outflow end 2716 of the stent 2702. Similar to the stent 102, the outflow end 2716 of the stent 2702 has a total of six endmost outflow crowns 2720A.

The transition portion 2724 bridges, connects, or otherwise extends between the inflow portion 2708 and the outflow portion 2718. The transition portion 2724 includes a total of six axial frame members 2752, each axial frame member 2752 extending between a crown 2720 of the outflow portion 2718 and two crowns 2710 of the inflow portion 2708. Each axial frame member 2752 includes two spaced apart legs 2756A, 2756B that radially and longitudinally extend from an outflow crown 2720 of the outflow portion 2718. Each leg 2756A, 2756B is further attached to a crown 2710 of the inflow portion 2708. Stated another way, each leg 2756A, 2756B is an angled segment extending between an outflow crown 2720 of the outflow portion 2718 and a crown 2710 of the inflow portion 2708. Each axial frame member 2752 is disposed approximately halfway between a pair of adjacent endmost outflow crowns 2720A. Three of the six axial frame members 2752 are commissure posts 2752A and aligned with and attached to a respective commissure of the three leaflets 134 of the prosthetic valve 132. Three of the axial frame members 2752 are axial struts 2752B and are disposed between adjacent commissure posts 2752A.

In this embodiment, the endmost outflow crowns 2720A are not connected to the axial frame members 2752 but rather may be considered to be free or unattached while the remaining outflow crowns 2720 of the outflow portion 2718 are connected to the axial frame members 2752 and disposed closer to the inflow end 2706 than the endmost outflow crowns 2720A. In the embodiment shown, there is a single row of struts 2722 and crowns 2720 coupled to the axial frame members 2752 and defining the outflow end 2716 of the stent 2702. Further, in the embodiment shown, exactly two struts 2722 and a single crown 2720 of the outflow portion 2718 are disposed between adjacent axial frame members 2752. Such an arrangement provides a series of six endmost outflow side openings 2725 formed at the outflow portion 2718 of the stent 2702. Each endmost outflow side opening 2725 is defined by two adjacent struts 2722 of the outflow portion 2718, two adjacent struts 2712 of the inflow portion 2708, and two adjacent axial frame members 2752 of the transition portion 2724. The endmost outflow side openings 2725 of the outflow portion 2718 are relatively larger than a plurality of side openings 2714 of the inflow portion 2708 to improve access to the coronary arteries. More particularly, the endmost outflow side openings 2725 of the outflow portion 2718 are configured to be of sufficient size to be easily crossed with a coronary guide catheter into either the right coronary artery or the left main coronary artery once the transcatheter valve prosthesis is deployed in situ.

As described above, the transition portion 2724 of the stent 2702 is configured for attachment to commissures of the prosthetic valve. FIG. 29 illustrates the transcatheter valve prosthesis 2700 in an expanded configuration, the transcatheter valve prosthesis 2700 including the stent 2702. As shown on FIG. 29, a material flap 2758 is attached to three commissure posts 2752A. Stated another way, stent 2702 includes a total of three material flaps 2758. The three material flaps 2758 are aligned with and attached to a respective commissure of the three leaflets of the prosthetic valve. In an embodiment, each material flap 2758 is generally diamond-shaped. Each material flap 2758 spans or bridges between legs 2756A, 2756B and two adjacent struts 2712 of the inflow portion 2708. In this embodiment, the entire perimeter of each material flap 2758 is connected to the stent 2702. The material flap 2758 may be formed from a material such as those suitable for graft material 144, such as but not limited to a natural or biological material such as pericardium or another membranous tissue such as intestinal submucosa, a low-porosity woven fabric, such as polyester, Dacron fabric, or PTFE, or a knit or woven polyester, such as a polyester or PTFE knit.

Each material flap 2758 forms a webbing or pad to which a respective commissure of the three leaflets of the prosthetic valve is attached. Since the three material flaps 2758 are aligned with and attached to a respective commissure of the three leaflets of the prosthetic valve, the material flaps 2758 aid in valve alignment and coaptation. Further, in an embodiment, each material flap 2758 may function like a trampoline and absorb shock during diastole. By functioning as a shock absorber, the material flaps 2758 prevent tissue damage, reduce paravalvular leakage, and increase the durability of the prosthetic valve.

In this embodiment, the inflow portion 2708 includes exactly four rows of struts 2712 and crowns 2710 between the axial frame members 2752 and the inflow end 2706 of the stent 2702. Further, in this embodiment, two struts 2712 and one crown 2710 are disposed between adjacent axial frame members 2752.

According to a first embodiment hereof, a transcatheter valve prosthesis includes a stent having a crimped configuration for delivery within a vasculature and an expanded configuration for deployment within a native heart valve. The stent is balloon expandable and includes an inflow portion, an outflow portion, and a transition portion extending between the inflow portion and the outflow portion. The inflow portion is formed proximate to an inflow end of the stent. The inflow portion includes a plurality of crowns and a plurality of struts with each crown being formed between a pair of opposing struts, a plurality of side openings being defined by the plurality of crowns and the plurality of struts. Endmost inflow side openings and endmost inflow crowns are formed at the inflow end of the stent. The inflow end of the stent has a total of twelve endmost inflow crowns. The outflow portion is formed proximate to an outflow end of the stent. The outflow portion includes a plurality of crowns and a plurality of struts with each crown being formed between a pair of opposing struts. Endmost outflow crowns are formed at the outflow end of the stent. The outflow end of the stent has a total of six endmost outflow crowns. A diameter of the inflow end of the stent is the same as a diameter of the outflow end of the stent. A prosthetic valve is disposed within and secured to at least the transition portion of the stent, the prosthetic valve being configured to block blood flow in one direction to regulate blood flow through a central lumen of the stent.

In an aspect of the first embodiment, and in combination with any other aspects herein, the prosthetic valve includes three leaflets and three commissures, each commissure being formed by attached adjacent lateral ends of an adjoining pair of the three leaflets.

In an aspect of the first embodiment, and in combination with any other aspects herein, the transition portion includes a total of six axial frame members, each axial frame member extending between a crown of the outflow portion and a crown of the inflow portion and each axial frame member disposed approximately halfway between a pair of adjacent endmost outflow crowns. Three of the six axial frame members are aligned with and attached to a respective commissure of the three leaflets of the prosthetic valve.

In an aspect of the first embodiment, and in combination with any other aspects herein, the three leaflets are attached to the stent along a margin of attachment that follows struts and nodes of the inflow portion of the stent, a node being defined as a region where two crowns of the plurality of crowns within the inflow portion connect. The margin of attachment has a smooth concave shape. The two crowns that connect at each node overlap.

In an aspect of the first embodiment, and in combination with any other aspects herein, struts adjacent to the six endmost outflow crowns are endmost struts and a plurality of holes are formed within the endmost struts. The plurality of holes are configured to attach a respective commissure of the three leaflets of the prosthetic valve to the stent.

In an aspect of the first embodiment, and in combination with any other aspects herein, the transition region is formed by a connection between abutting crowns of the outflow portion and crowns of the inflow portion, the connection having an increased width relative to the plurality of struts of the outflow portion. A generally triangular material flap is attached to the plurality of holes and the respective commissure of the three leaflets of the prosthetic valve is attached to the generally triangular material flap.

In an aspect of the first embodiment, and in combination with any other aspects herein, the transition portion includes a total of six axial frame members, each axial frame member including a planar base and two spaced apart legs longitudinally extending from the planar base, the planar base having an increased width relative to the plurality of struts of the outflow portion and each leg being attached to a crown of the inflow portion. The legs radially extend from the planar base when the stent is in the expanded configuration. Further, a generally diamond-shaped material flap is attached to three of the axial frame members and the respective commissure of the three leaflets of the prosthetic valve is attached to the generally diamond-shaped material flap.

In an aspect of the first embodiment, and in combination with any other aspects herein, the transition portion includes a total of six axial frame members, each axial frame member including two spaced apart legs radially and longitudinally extending from a crown of the outflow portion, each leg being attached to a crown of the inflow portion.

In an aspect of the first embodiment, and in combination with any other aspects herein, a generally diamond-shaped material flap is attached to three of the axial frame members and the respective commissure of the three leaflets of the prosthetic valve is attached to the generally diamond-shaped material flap.

In an aspect of the first embodiment, and in combination with any other aspects herein, struts of the inflow portion alternate between a first thickness and a second thickness, the second thickness being greater than the first thickness.

In an aspect of the first embodiment, and in combination with any other aspects herein, the transition portion includes a total of six axial frame members, each axial frame member attached to a respective endmost outflow crown.

In an aspect of the first embodiment, and in combination with any other aspects herein, a height of the stent in the expanded configuration is between 12 and 18 mm, the height being measured between the endmost inflow crowns the endmost outflow crowns.

In an aspect of the first embodiment, and in combination with any other aspects herein, the stent is configured for intra-annular placement within a native aortic valve.

In an aspect of the first embodiment, and in combination with any other aspects herein, the inflow portion is tubular and the outflow portion is a ring.

In an aspect of the first embodiment, and in combination with any other aspects herein, the transition portion includes a total of six axial frame members and a total of six endmost outflow side openings are formed at the outflow end of the stent, each endmost outflow side opening being defined by two struts of the outflow portion, four struts of the inflow portion, and two axial frame members of the transition portion. Each endmost outflow side opening is heart-shaped.

In an aspect of the first embodiment, and in combination with any other aspects herein, at least one strut of the inflow portion is tapered and the thickness varies along a length thereof such that a middle portion is relatively thinner than opposing end portions of the strut.

According to a second embodiment hereof, a transcatheter valve prosthesis includes a stent having a crimped configuration for delivery within a vasculature and an expanded configuration for deployment within a native heart valve. The stent is balloon expandable. The stent includes an inflow portion and an outflow portion. The inflow portion is formed proximate to an inflow end of the stent. The inflow portion includes a plurality of crowns and a plurality of struts with each crown being formed between a pair of opposing struts, a plurality of side openings being defined by the plurality of crowns and the plurality of struts. Endmost inflow side openings and endmost inflow crowns are formed at the inflow end of the stent and the inflow end of the stent has a total of twelve endmost inflow crowns. The outflow portion is formed proximate to an outflow end of the stent. The outflow end of the stent has a total of three commissure posts, each commissure post longitudinally extending from a crown of the inflow end and the three commissure posts being circumferentially spaced apart. A diameter of the inflow end of the stent is the same as a diameter of the outflow end of the stent. A prosthetic valve is disposed within and secured to at least the outflow portion of the stent, the prosthetic valve being configured to block blood flow in one direction to regulate blood flow through a central lumen of the stent.

In an aspect of the second embodiment, and in combination with any other aspects herein, the prosthetic valve includes three leaflets and three commissures, each commissure being formed by attached adjacent lateral ends of an adjoining pair of the three leaflets. The three commissure posts are aligned with and attached to a respective commissure of the three leaflets of the prosthetic valve.

In an aspect of the second embodiment, and in combination with any other aspects herein, the three leaflets are attached to the stent along a margin of attachment that follows struts and nodes of the inflow portion of the stent, a node being defined as a region where two crowns of the plurality of crowns within the inflow portion connect. The margin of attachment has a smooth concave shape. The two crowns that connect at each node overlap.

In an aspect of the second embodiment, and in combination with any other aspects herein, each commissure post is a planar bar.

In an aspect of the second embodiment, and in combination with any other aspects herein, each commissure post is u-shaped with an apex and two spaced apart legs longitudinally extending from the apex, each leg being attached to a crown of the inflow portion. The legs radially extend from the apex when the stent is in the expanded configuration.

In an aspect of the second embodiment, and in combination with any other aspects herein, struts of the inflow portion alternate between a first thickness and a second thickness, the second thickness being greater than the first thickness.

In an aspect of the second embodiment, and in combination with any other aspects herein, a height of the stent in the expanded configuration is between 12 and 18 mm, the height being measured between the endmost inflow crowns the endmost outflow crowns.

In an aspect of the second embodiment, and in combination with any other aspects herein, the stent is configured for intra-annular placement within a native aortic valve.

In an aspect of the second embodiment, and in combination with any other aspects herein, at least one strut of the inflow portion is tapered and the thickness varies along a length thereof such that a middle portion is relatively thinner than opposing end portions of the strut.

According to a third embodiment hereof, a transcatheter valve prosthesis includes a stent having a crimped configuration for delivery within a vasculature and an expanded configuration for deployment within a native heart valve. The stent is balloon expandable. The stent includes a plurality of axial frame members, an inflow portion, and an outflow portion. The inflow portion includes at least three rows of struts and crowns formed between adjacent pairs of said struts. The at least three rows of the inflow portion are formed between an inflow end of the axial frame members and an inflow end of the stent. The outflow portion includes a single row of struts and crowns formed between adjacent pair of said struts. The outflow portion is coupled to an outflow end of the axial frame members. Exactly two struts of the plurality of struts of the outflow portion are disposed between adjacent axial frame members.

In an aspect of the third embodiment, and in combination with any other aspects herein, the plurality of axial frame members includes exactly six axial frame members, three of the six axial frame members are commissure posts and three of the six axial frame members are axial struts, and each of the axial struts is disposed between adjacent commissure posts. The transcatheter valve prosthesis further includes a prosthetic valve including three leaflets, and each commissure of the leaflets is coupled to a corresponding commissure post of the stent.

In an aspect of the third embodiment, and in combination with any other aspects herein, one of the at least three rows of struts and crowns of the inflow portion includes crowns coupled to inflow end of the axial frame member. The one row includes at least four struts between adjacent axial frame members.

In an aspect of the third embodiment, and in combination with any other aspects herein, the one row includes exactly four struts between adjacent axial frame members.

In an aspect of the third embodiment, and in combination with any other aspects herein, the inflow portion includes exactly three rows of a plurality of struts and crowns.

In an aspect of the third embodiment, and in combination with any other aspects herein, the plurality of axial frame members includes a plurality of axial struts and a plurality of commissure posts. There are the same number of axial struts and commissure posts, and each of the axial struts is disposed between adjacent commissure posts. The transcatheter valve prosthesis further includes a prosthetic valve including a plurality of leaflets, and each commissure of the leaflets is coupled to a corresponding commissure post of the stent.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A transcatheter valve prosthesis comprising:
a stent having a crimped configuration for delivery within a vasculature and an expanded configuration for deployment within a native heart valve, wherein the stent is balloon expandable, the stent including
an inflow portion formed proximate to an inflow end of the stent, the inflow portion including a plurality of crowns and a plurality of struts with each crown being formed between a pair of opposing struts, a plurality of side openings being defined by the plurality of crowns and the plurality of struts, wherein endmost inflow side openings and endmost inflow crowns are formed at the inflow end of the stent and the inflow end of the stent has a total of twelve endmost inflow crowns,
an outflow portion formed proximate to an outflow end of the stent, the outflow portion including a plurality of crowns and a plurality of struts with each crown being formed between a pair of opposing struts, wherein endmost outflow crowns are formed at the outflow end of the stent and the outflow end of the stent has a total of six endmost outflow crowns, and wherein a diameter of the inflow end of the stent is the same as a diameter of the outflow end of the stent, and
a transition portion extending between the inflow portion and the outflow portion, wherein the transition portion includes a total of six axial frame members and a total of six endmost outflow side openings are formed at the outflow end of the stent, each endmost outflow side opening being defined by two struts of the outflow portion, four struts of the inflow portion, and two axial frame members of the transition portion, and a prosthetic valve disposed within and secured to at least the transition portion of the stent, the prosthetic valve being configured to block blood flow in one direction to regulate blood flow through a central lumen of the stent.

2. The transcatheter valve prosthesis of claim 1, wherein the prosthetic valve includes three leaflets and three commissures, each commissure being formed by attached adjacent lateral ends of an adjoining pair of the three leaflets.

3. The transcatheter valve prosthesis of claim 2, wherein each axial frame member extends between a crown of the outflow portion and a crown of the inflow portion and each axial frame member disposed approximately halfway between a pair of adjacent endmost outflow crowns, and wherein three of the six axial frame members are aligned with and attached to a respective commissure of the three leaflets of the prosthetic valve.

4. The transcatheter valve prosthesis of claim 2, wherein the three leaflets are attached to the stent along a margin of attachment that follows struts and nodes of the inflow portion of the stent, a node being defined as a region where two crowns of the plurality of crowns within the inflow portion connect, wherein the margin of attachment has a smooth concave shape and wherein the two crowns that connect at each node overlap.

5. The transcatheter valve prosthesis of claim 2, wherein struts adjacent to the six endmost outflow crowns are endmost struts and a plurality of holes are formed within the endmost struts, the plurality of holes configured to attach a respective commissure of the three leaflets of the prosthetic valve to the stent.

6. The transcatheter valve prosthesis of claim 5, wherein the transition region is formed by a connection between abutting crowns of the outflow portion and crowns of the inflow portion, the connection having an increased width relative to the plurality of struts of the outflow portion.

7. The transcatheter valve prosthesis of claim 5, wherein a generally triangular material flap is attached to the plurality of holes and the respective commissure of the three leaflets of the prosthetic valve is attached to the generally triangular material flap.

8. The transcatheter valve prosthesis of claim 1, wherein each axial frame member is attached to a respective endmost outflow crown.

9. The transcatheter valve prosthesis of claim 1, wherein at least one strut of the inflow portion is tapered and the thickness varies along a length thereof such that a middle portion is relatively thinner than opposing end portions of the strut.

10. A transcatheter valve prosthesis comprising:
a stent having a crimped configuration for delivery within a vasculature and an expanded configuration for deployment within a native heart valve, wherein the stent is balloon expandable, the stent including
a plurality of axial frame members, each axial frame member having an inflow end and an outflow end,
an inflow portion including at least three rows of struts and crowns formed between adjacent pairs of said struts, wherein the at least three rows of the inflow portion are formed between the inflow ends of the axial frame members and an inflow end of the stent, and
an outflow portion including a single row of struts and crowns formed between adjacent pair of said struts, the outflow portion being coupled to the outflow ends of the axial frame members, wherein exactly two struts of the plurality of struts of the outflow portion are disposed between adjacent axial frame members, and
wherein each of the axial frame members extends between the inflow portion and the outflow portion of the stent and at least one of the axial frame members is a commissure post.

11. The transcatheter valve prosthesis of claim 10,
wherein the plurality of axial frame members includes exactly six axial frame members,
wherein three of the six axial frame members are commissure posts and three of the six axial frame members are axial struts, and
wherein each of the axial struts is disposed between adjacent commissure posts.

12. The transcatheter valve prosthesis of claim 11, further compering a prosthetic valve including three leaflets, wherein each commissure of the leaflets is coupled to a corresponding commissure post of the stent.

13. The transcatheter valve prosthesis of claim 10, wherein one of the at least three rows of struts and crowns of the inflow portion includes crowns coupled to the inflow end of the axial frame member, wherein the one row includes exactly four struts between adjacent axial frame members.

* * * * *